US010080821B2

(12) United States Patent
Kangas et al.

(10) Patent No.: US 10,080,821 B2
(45) Date of Patent: Sep. 25, 2018

(54) NUCLEATION OF DRUG DELIVERY BALLOONS TO PROVIDE IMPROVED CRYSTAL SIZE AND DENSITY

(75) Inventors: Steve Kangas, Woodbury, MN (US); Michael Sean Owens, Richfield, MN (US); Jon Patterson, St. Louis Park, MN (US); Dave Ekberg, St. Michael, MN (US); Erik Haun, Coon Rapids, MN (US); Eric Henderson, Champlin, MN (US); Aaron Foss, Plymouth, MN (US); Yen-Lane Chen, New Brighton, MN (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 1029 days.

(21) Appl. No.: 12/815,138

(22) Filed: Jun. 14, 2010

(65) Prior Publication Data
US 2011/0015664 A1  Jan. 20, 2011

Related U.S. Application Data

(60) Provisional application No. 61/271,167, filed on Jul. 17, 2009.

(51) Int. Cl.
*A61L 29/16* (2006.01)
*A61L 29/06* (2006.01)

(52) U.S. Cl.
CPC .............. *A61L 29/16* (2013.01); *A61L 29/06* (2013.01); *A61L 2300/416* (2013.01); *A61L 2300/606* (2013.01); *A61L 2300/622* (2013.01); *A61L 2300/63* (2013.01)

(58) Field of Classification Search
CPC combination set(s) only.
See application file for complete search history.

(56) References Cited

U.S. PATENT DOCUMENTS

| | | |
|---|---|---|
| 304,121 A | 8/1884 | Munch |
| 2,098,381 A | 11/1937 | Fine |
| 4,026,296 A | 5/1977 | Stoy |
| 4,186,745 A | 2/1980 | Lewis |
| 4,364,392 A | 12/1982 | Strother et al. |
| 4,481,323 A | 11/1984 | Sterling |
| 4,490,421 A | 12/1984 | Levy |
| 4,515,593 A | 5/1985 | Norton |
| 4,589,873 A | 5/1986 | Schwartz |
| 4,603,152 A | 7/1986 | Laurin |
| 4,644,936 A | 2/1987 | Schiff |
| 4,693,243 A | 9/1987 | Buras |
| 4,733,665 A | 3/1988 | Palmaz |
| 4,769,013 A | 9/1988 | Lorenz |
| 4,784,647 A | 11/1988 | Gross |
| 4,796,629 A | 1/1989 | Grayzel |
| 4,800,882 A | 1/1989 | Gianturco |
| 4,886,062 A | 12/1989 | Wiktor |
| 4,906,244 A | 3/1990 | Pinchuk et al. |
| 4,931,583 A | 6/1990 | Hull et al. |
| 4,950,239 A | 8/1990 | Gahara |
| 4,950,256 A | 8/1990 | Luther |
| 4,994,033 A | 2/1991 | Shockey et al. |
| 5,026,607 A | 6/1991 | Kiezulas |
| 5,027,996 A | 7/1991 | Fefeu |
| 5,041,100 A | 8/1991 | Rowland |
| 5,049,131 A | 9/1991 | Deuss |
| 5,087,244 A | 2/1992 | Wolinsky et al. |
| 5,091,205 A | 2/1992 | Fan |
| 5,092,841 A | 3/1992 | Spears |
| 5,098,381 A | 3/1992 | Schneider |
| 5,102,402 A | 4/1992 | Dror et al. |
| 5,135,516 A | 8/1992 | Sahatjian |
| 5,169,933 A | 12/1992 | Anderson |
| 5,180,366 A | 1/1993 | Woods |
| 5,199,951 A | 4/1993 | Spears |
| 5,213,576 A | 5/1993 | Abiuso et al. |
| 5,213,580 A | 5/1993 | Slepian et al. |
| 5,232,444 A | 8/1993 | Just et al. |
| 5,236,413 A | 8/1993 | Feiring |
| 5,250,069 A | 10/1993 | Nobuyoshi |
| 5,264,260 A | 11/1993 | Saab |
| 5,270,086 A | 12/1993 | Hamlin |
| 5,282,785 A | 2/1994 | Shapland et al. |
| 5,286,254 A | 2/1994 | Shapland et al. |
| 5,295,962 A | 3/1994 | Crocker et al. |
| 5,304,121 A | 4/1994 | Sahatjian |
| 5,318,531 A | 6/1994 | Leone |
| 5,320,634 A | 6/1994 | Vigil |
| 5,324,261 A | 6/1994 | Amundson et al. |
| 5,328,468 A | 7/1994 | Kaneko |
| 5,328,471 A | 7/1994 | Slepian |
| 5,342,628 A | 8/1994 | Picha |
| 5,344,400 A | 9/1994 | Kaneko |
| 5,344,402 A | 9/1994 | Crocker |
| 5,362,831 A | 11/1994 | Mongelli |
| 5,368,566 A | 11/1994 | Crocker |
| 5,370,614 A | 12/1994 | Amundson et al. |
| 5,380,299 A | 1/1995 | Fearnot |
| 5,383,928 A | 1/1995 | Scott |
| 5,385,152 A | 1/1995 | Abele |

(Continued)

FOREIGN PATENT DOCUMENTS

| | | |
|---|---|---|
| CA | 2363119 | 8/2000 |
| DE | 19908318 | 8/2000 |

(Continued)

OTHER PUBLICATIONS

Kleeman, R.D., "Relation Between the Surface Tension and Relative Density of a Liquid," Science, 1924, vol. 60, No. 1565, p. 589.*

(Continued)

*Primary Examiner* — Dennis J Parad
(74) *Attorney, Agent, or Firm* — Seager, Tufte & Wickhem, LLP

(57) ABSTRACT

Drug delivery balloons have densely packed crystals of small particle size of the drug thereon. An amorphous drug coating is applied to a balloon surface and annealed to provide the crystals. The balloon surface is nucleated to induce formation of drug crystals in the annealing step to provide the crystals in high density with small size.

17 Claims, 9 Drawing Sheets

(56) References Cited

U.S. PATENT DOCUMENTS

| | | |
|---|---|---|
| 5,405,472 A | 4/1995 | Leone |
| 5,419,760 A | 5/1995 | Narciso |
| 5,421,826 A | 6/1995 | Crocker et al. |
| 5,425,703 A | 6/1995 | Feiring |
| 5,427,767 A | 6/1995 | Kresse |
| 5,439,446 A | 8/1995 | Barry |
| 5,443,496 A | 8/1995 | Schwartz |
| 5,447,724 A | 9/1995 | Helmus |
| 5,449,382 A | 9/1995 | Dayton |
| 5,464,650 A | 11/1995 | Berg |
| 5,470,307 A | 11/1995 | Lindall |
| 5,489,525 A | 2/1996 | Pastan |
| 5,498,238 A | 3/1996 | Shapland et al. |
| 5,499,971 A | 3/1996 | Shapland et al. |
| 5,500,180 A | 3/1996 | Anderson |
| 5,542,926 A | 8/1996 | Crocker |
| 5,545,208 A | 8/1996 | Wolff |
| 5,549,603 A | 8/1996 | Feiring |
| 5,554,119 A | 9/1996 | Harrison et al. |
| 5,554,182 A | 9/1996 | Dinh |
| 5,556,383 A | 9/1996 | Wang et al. |
| 5,558,642 A | 9/1996 | Schweich, Jr. et al. |
| 5,562,922 A | 10/1996 | Lambert |
| 5,569,184 A | 10/1996 | Crocker et al. |
| 5,569,463 A | 10/1996 | Helmus |
| 5,571,089 A | 11/1996 | Crocker |
| 5,578,075 A | 11/1996 | Dayton |
| 5,588,962 A | 12/1996 | Nicholas et al. |
| 5,599,306 A | 2/1997 | Klein et al. |
| 5,599,307 A | 2/1997 | Bacher et al. |
| 5,609,629 A | 3/1997 | Fearnot et al. |
| 5,611,775 A | 3/1997 | Machold et al. |
| 5,616,149 A | 4/1997 | Barath |
| 5,624,411 A | 4/1997 | Tuch |
| 5,626,862 A | 5/1997 | Brem |
| 5,628,730 A | 5/1997 | Shapland et al. |
| 5,629,008 A | 5/1997 | Lee |
| 5,634,901 A | 6/1997 | Alba |
| 5,637,086 A | 6/1997 | Ferguson et al. |
| 5,651,986 A | 7/1997 | Brem |
| 5,665,772 A | 9/1997 | Cottens |
| 5,669,874 A | 9/1997 | Feiring |
| 5,674,192 A | 10/1997 | Sahatjian et al. |
| 5,674,241 A | 10/1997 | Bley |
| 5,679,400 A | 11/1997 | Tuch |
| 5,685,847 A | 11/1997 | Barry |
| 5,688,516 A | 11/1997 | Raad |
| 5,693,034 A | 12/1997 | Buscemi et al. |
| 5,697,967 A | 12/1997 | Dinh |
| 5,704,908 A | 1/1998 | Hofmann et al. |
| 5,707,385 A | 1/1998 | Williams |
| 5,716,981 A | 2/1998 | Hunter |
| 5,728,066 A | 3/1998 | Daneshvar |
| 5,733,925 A | 3/1998 | Kunz |
| 5,766,158 A | 6/1998 | Opolski |
| 5,769,883 A | 6/1998 | Buscemi |
| 5,797,877 A | 8/1998 | Hamilton |
| 5,800,538 A | 9/1998 | Slepian et al. |
| 5,807,306 A | 9/1998 | Shapland et al. |
| 5,810,763 A | 9/1998 | Feiring |
| 5,833,657 A | 11/1998 | Reinhardt et al. |
| 5,833,658 A | 11/1998 | Levy |
| 5,843,089 A | 12/1998 | Sahatjian et al. |
| 5,854,382 A | 12/1998 | Loomis |
| 5,855,546 A | 1/1999 | Hastings |
| 5,857,998 A | 1/1999 | Barry |
| 5,865,801 A | 2/1999 | Houser |
| 5,868,719 A | 2/1999 | Tsukernik |
| 5,869,127 A | 2/1999 | Zhong |
| 5,876,374 A | 3/1999 | Alba |
| 5,893,840 A | 4/1999 | Hull et al. |
| 5,900,246 A | 5/1999 | Lambert |
| 5,902,266 A | 5/1999 | Leone |
| 5,902,299 A | 5/1999 | Jayaraman |
| 5,928,279 A | 7/1999 | Shannon |
| 5,935,275 A | 8/1999 | Burgard |
| 5,935,506 A | 8/1999 | Schmitz |
| 5,947,977 A | 9/1999 | Slepian et al. |
| 5,954,693 A | 9/1999 | Barry |
| 5,954,706 A | 9/1999 | Sahatjian |
| 5,977,163 A | 11/1999 | Li |
| 5,981,568 A | 11/1999 | Kunz et al. |
| 6,048,356 A | 4/2000 | Ravenscroft et al. |
| 6,048,515 A | 4/2000 | Kresse |
| 6,048,620 A | 4/2000 | Zhong |
| 6,099,454 A | 8/2000 | Hastings |
| 6,099,926 A | 8/2000 | Thakrar |
| 6,129,705 A | 10/2000 | Grantz |
| 6,142,973 A | 11/2000 | Carleton |
| 6,146,356 A | 11/2000 | Wang et al. |
| 6,146,358 A | 11/2000 | Rowe |
| 6,183,658 B1 | 2/2001 | Lesniak |
| 6,186,745 B1 | 2/2001 | Johnson |
| 6,195,583 B1 | 2/2001 | Feiring |
| 6,203,551 B1 | 3/2001 | Wu |
| 6,218,016 B1 | 4/2001 | Tedeschi et al. |
| 6,219,577 B1 | 4/2001 | Brown, III et al. |
| 6,240,407 B1 | 5/2001 | Chang |
| 6,245,103 B1 | 6/2001 | Stinson |
| 6,262,107 B1 | 7/2001 | Li |
| 6,270,522 B1 | 8/2001 | Simhambhatla |
| 6,280,411 B1 | 8/2001 | Lennox |
| 6,283,947 B1 | 9/2001 | Mirzaee |
| 6,287,332 B1 | 9/2001 | Bolz |
| 6,296,619 B1 | 10/2001 | Brisken et al. |
| 6,299,604 B1 | 10/2001 | Ragheb |
| 6,306,166 B1 | 10/2001 | Barry et al. |
| 6,344,028 B1 | 2/2002 | Barry |
| 6,355,029 B1 | 3/2002 | Joye |
| 6,364,856 B1 | 4/2002 | Ding et al. |
| 6,364,893 B1 | 4/2002 | Sahatjian et al. |
| 6,369,039 B1 | 4/2002 | Palasis et al. |
| 6,389,314 B2 | 5/2002 | Feiring |
| 6,391,033 B2 | 5/2002 | Ryan |
| 6,398,708 B1 | 6/2002 | Hastings |
| 6,409,716 B1 | 6/2002 | Sahatjian et al. |
| 6,418,448 B1 | 7/2002 | Sarkar |
| 6,419,692 B1 | 7/2002 | Yang et al. |
| 6,428,534 B1 | 8/2002 | Joye et al. |
| 6,432,102 B2 | 8/2002 | Joye |
| 6,440,990 B1 | 8/2002 | Cottens |
| 6,443,941 B1 | 9/2002 | Slepian et al. |
| 6,451,373 B1 | 9/2002 | Hossainy |
| 6,468,297 B1 | 10/2002 | Williams |
| 6,494,862 B1 | 12/2002 | Ray |
| 6,506,408 B1 | 1/2003 | Palasis |
| 6,511,477 B2 | 1/2003 | Altman |
| 6,514,245 B1 | 2/2003 | Williams |
| 6,524,274 B1 | 2/2003 | Rosenthal et al. |
| 6,527,740 B1 | 3/2003 | Jackson |
| 6,537,194 B1 | 3/2003 | Winkler |
| 6,541,039 B1 | 4/2003 | Lesniak |
| 6,544,221 B1 | 4/2003 | Kokish et al. |
| 6,544,223 B1 | 4/2003 | Kokish |
| 6,545,097 B2 | 4/2003 | Pinchuk et al. |
| 6,548,569 B1 | 4/2003 | Williams |
| 6,582,353 B1 | 6/2003 | Hastings |
| 6,585,926 B1 | 7/2003 | Mirzaee |
| 6,592,548 B2 | 7/2003 | Jayaraman |
| 6,602,246 B1 | 8/2003 | Joye |
| 6,616,650 B1 | 9/2003 | Rowe |
| 6,623,452 B2 | 9/2003 | Chien et al. |
| 6,623,749 B2 | 9/2003 | Williams |
| 6,638,246 B1 | 10/2003 | Naimark et al. |
| 6,645,135 B1 | 11/2003 | Bhat |
| 6,648,879 B2 | 11/2003 | Joye |
| 6,656,156 B2 | 12/2003 | Yang et al. |
| 6,663,880 B1 | 12/2003 | Roorda et al. |
| 6,682,545 B1 | 1/2004 | Kester |
| 6,685,648 B2 | 2/2004 | Flaherty |
| 6,699,272 B2 | 3/2004 | Slepian et al. |
| 6,706,013 B1 | 3/2004 | Bhat et al. |
| 6,730,105 B2 | 5/2004 | Shiber |
| 6,733,474 B2 | 5/2004 | Kusleika |

(56) References Cited

U.S. PATENT DOCUMENTS

| | | |
|---|---|---|
| 6,780,324 B2 | 8/2004 | Le Garrec et al. |
| 6,783,543 B2 | 8/2004 | Jang |
| 6,786,900 B2 | 9/2004 | Joye |
| 6,786,901 B2 | 9/2004 | Joye |
| 6,790,224 B2 | 9/2004 | Gerberding |
| 6,796,960 B2 | 9/2004 | Cioanta et al. |
| 6,805,898 B1 | 10/2004 | Wu |
| 6,811,550 B2 | 11/2004 | Holland |
| 6,838,493 B2 | 1/2005 | Williams |
| 6,858,644 B2 | 2/2005 | Benigni et al. |
| 6,863,861 B1 | 3/2005 | Zhang (Ken) |
| 6,867,247 B2 | 3/2005 | Williams |
| 6,890,339 B2 | 5/2005 | Sahatjian et al. |
| 6,890,583 B2 | 5/2005 | Chudzik et al. |
| 6,899,731 B2 | 5/2005 | Li et al. |
| 6,908,462 B2 | 6/2005 | Joye |
| 6,918,927 B2 | 7/2005 | Bates |
| 6,923,996 B2 | 8/2005 | Epstein et al. |
| 6,939,320 B2 | 9/2005 | Lennox |
| 6,942,680 B2 | 9/2005 | Grayzel |
| 6,955,661 B1 | 10/2005 | Herweck et al. |
| 6,960,346 B2 | 11/2005 | Shukla |
| 6,972,015 B2 | 12/2005 | Joye |
| 6,991,647 B2 | 1/2006 | Jadhav |
| 6,995,661 B2 | 2/2006 | Amari |
| 7,005,414 B2 | 2/2006 | Barnikol |
| 7,008,979 B2 | 3/2006 | Schottman et al. |
| 7,018,371 B2 | 3/2006 | Forman |
| 7,037,319 B2 | 5/2006 | Weber |
| 7,048,714 B2 | 5/2006 | Richter |
| 7,056,533 B2 | 6/2006 | Chudzik et al. |
| 7,060,051 B2 | 6/2006 | Palasis |
| 7,060,062 B2 | 6/2006 | Joye |
| 7,066,904 B2 | 6/2006 | Rosenthal et al. |
| 7,070,576 B2 | 7/2006 | Obrien |
| 7,081,112 B2 | 7/2006 | Joye |
| 7,090,655 B2 | 8/2006 | Barry |
| 7,105,175 B2 | 9/2006 | Schwarz |
| 7,108,684 B2 | 9/2006 | Farnan |
| 7,115,299 B2 | 10/2006 | Kokish |
| 7,150,738 B2 | 12/2006 | Ray |
| 7,160,317 B2 | 1/2007 | McHale |
| 7,166,098 B1 | 1/2007 | Steward et al. |
| 7,179,251 B2 | 2/2007 | Palasis |
| 7,232,486 B2 | 6/2007 | Keri |
| 7,241,455 B2 | 7/2007 | Richard |
| 7,247,338 B2 | 7/2007 | Pui |
| 7,279,002 B2 | 10/2007 | Shaw |
| 7,303,572 B2 | 12/2007 | Melsheimer |
| 7,306,625 B1 | 12/2007 | Stratford |
| 7,323,189 B2 | 1/2008 | Pathak |
| 7,335,184 B2 | 2/2008 | Laguna |
| 7,357,940 B2 | 4/2008 | Richard et al. |
| 7,364,585 B2 | 4/2008 | Weber |
| 7,371,257 B2 | 5/2008 | Sahatjian et al. |
| 7,381,418 B2 | 6/2008 | Richard |
| 7,393,685 B1 | 7/2008 | Jordan |
| 7,402,172 B2 | 7/2008 | Chin et al. |
| 7,407,671 B2 | 8/2008 | McBride et al. |
| 7,407,684 B2 | 8/2008 | Spencer et al. |
| 7,459,169 B2 | 12/2008 | Nilsson et al. |
| 7,462,165 B2 | 12/2008 | Ding et al. |
| 7,470,252 B2 | 12/2008 | Mickley et al. |
| 7,473,242 B2 | 1/2009 | Donovan et al. |
| 7,491,188 B2 | 2/2009 | Holman et al. |
| 7,494,497 B2 | 2/2009 | Weber |
| 7,527,604 B2 | 5/2009 | Naimark |
| 7,553,292 B2 | 6/2009 | Kilpatrick et al. |
| 7,563,324 B1 | 7/2009 | Chen |
| 7,572,245 B2 | 8/2009 | Herweck et al. |
| 7,588,642 B1 | 9/2009 | Morris |
| 7,604,631 B2 | 10/2009 | Reynolds |
| 7,632,288 B2 | 12/2009 | Wu |
| 7,682,387 B2 | 3/2010 | Shulze et al. |
| 7,718,213 B1 | 5/2010 | Scheer |
| 7,731,685 B2 | 6/2010 | Ragheb |
| 7,744,644 B2 | 6/2010 | Weber et al. |
| 7,750,041 B2 | 7/2010 | Speck et al. |
| 7,753,876 B2 | 7/2010 | Cervantes |
| 7,758,892 B1 | 7/2010 | Chen et al. |
| 7,762,995 B2 | 7/2010 | Eversull |
| 7,767,219 B2 | 8/2010 | Weber et al. |
| 7,771,740 B2 | 8/2010 | Strickler et al. |
| 7,773,447 B2 | 8/2010 | Kajigaya |
| 7,794,751 B2 | 9/2010 | Chudzik et al. |
| 7,803,149 B2 | 9/2010 | Bates |
| 7,811,622 B2 | 10/2010 | Bates et al. |
| 8,291,854 B2 | 10/2012 | Behnisch |
| 2001/0020151 A1 | 9/2001 | Reed et al. |
| 2002/0010489 A1 | 1/2002 | Grayzel |
| 2002/0037358 A1 | 3/2002 | Barry et al. |
| 2002/0041898 A1 | 4/2002 | Unger |
| 2002/0042645 A1 | 4/2002 | Shannon |
| 2002/0151844 A1 | 10/2002 | Yang et al. |
| 2002/0183581 A1 | 12/2002 | Yoe et al. |
| 2003/0028210 A1 | 2/2003 | Boyle |
| 2003/0040712 A1 | 2/2003 | Ray et al. |
| 2003/0060877 A1 | 3/2003 | Falotico |
| 2003/0064965 A1 | 4/2003 | Richter |
| 2003/0077253 A1 | 4/2003 | Palasis |
| 2003/0083740 A1 | 5/2003 | Pathak |
| 2003/0114791 A1 | 6/2003 | Rosenthal et al. |
| 2003/0153870 A1 | 8/2003 | Meyer |
| 2003/0158517 A1 | 8/2003 | Kokish |
| 2003/0233068 A1 | 12/2003 | Jayaraman |
| 2003/0236513 A1 | 12/2003 | Schwarz et al. |
| 2003/0236514 A1 | 12/2003 | Schwarz |
| 2004/0023851 A1 | 2/2004 | Barnikol |
| 2004/0033251 A1 | 2/2004 | Sparer et al. |
| 2004/0034336 A1 | 2/2004 | Scott et al. |
| 2004/0039437 A1 | 2/2004 | Sparer et al. |
| 2004/0044308 A1 | 3/2004 | Naimark et al. |
| 2004/0044404 A1 | 3/2004 | Stucke et al. |
| 2004/0047911 A1 | 3/2004 | Lyu et al. |
| 2004/0059290 A1 | 3/2004 | Palasis |
| 2004/0064093 A1 | 4/2004 | Hektner et al. |
| 2004/0073284 A1 | 4/2004 | Bates et al. |
| 2004/0077948 A1 | 4/2004 | Violante et al. |
| 2004/0086550 A1 | 5/2004 | Roorda et al. |
| 2004/0086569 A1 | 5/2004 | Sparer et al. |
| 2004/0098014 A1 | 5/2004 | Flugelman et al. |
| 2004/0098108 A1 | 5/2004 | Harder |
| 2004/0111144 A1 | 6/2004 | Lawin |
| 2004/0115273 A1 | 6/2004 | Sparer et al. |
| 2004/0117222 A1 | 6/2004 | Rokosz |
| 2004/0127978 A1 | 7/2004 | Sparer et al. |
| 2004/0137066 A1 | 7/2004 | Jayaraman |
| 2004/0142011 A1 | 7/2004 | Nilsson et al. |
| 2004/0143287 A1 | 7/2004 | Konstantino |
| 2004/0175406 A1 | 9/2004 | Schwarz |
| 2004/0180039 A1 | 9/2004 | Toner et al. |
| 2004/0202691 A1 | 10/2004 | Richard |
| 2004/0210191 A1 | 10/2004 | Farnan |
| 2004/0215169 A1 | 10/2004 | Li |
| 2004/0219214 A1 | 11/2004 | Gravett et al. |
| 2004/0224003 A1 | 11/2004 | Schultz |
| 2004/0224080 A1 | 11/2004 | Epstein et al. |
| 2004/0230176 A1 | 11/2004 | Shanahan et al. |
| 2004/0234575 A1 | 11/2004 | Horres |
| 2004/0260239 A1 | 12/2004 | Kusleika |
| 2005/0015046 A1 | 1/2005 | Weber et al. |
| 2005/0025801 A1 | 2/2005 | Richard et al. |
| 2005/0025802 A1 | 2/2005 | Richard et al. |
| 2005/0025803 A1 | 2/2005 | Richard et al. |
| 2005/0025848 A1 | 2/2005 | Huang |
| 2005/0027283 A1 | 2/2005 | Richard et al. |
| 2005/0037048 A1 | 2/2005 | Song |
| 2005/0037050 A1 | 2/2005 | Weber |
| 2005/0043678 A1 | 2/2005 | Freyman |
| 2005/0055077 A1 | 3/2005 | Marco et al. |
| 2005/0060028 A1 | 3/2005 | Horres |
| 2005/0064005 A1 | 3/2005 | Dinh et al. |
| 2005/0064038 A1 | 3/2005 | Dinh et al. |
| 2005/0101522 A1 | 5/2005 | Speck et al. |

(56) References Cited

U.S. PATENT DOCUMENTS

| | | |
|---|---|---|
| 2005/0106206 A1 | 5/2005 | Herweck et al. |
| 2005/0129727 A1 | 6/2005 | Weber et al. |
| 2005/0129731 A1 | 6/2005 | Horres |
| 2005/0137618 A1 | 6/2005 | Kunis |
| 2005/0154416 A1 | 7/2005 | Herweck et al. |
| 2005/0158359 A1 | 7/2005 | Epstein et al. |
| 2005/0169969 A1 | 8/2005 | Li et al. |
| 2005/0176678 A1 | 8/2005 | Horres |
| 2005/0181015 A1 | 8/2005 | Zhong |
| 2005/0182361 A1 | 8/2005 | Lennox |
| 2005/0186248 A1* | 8/2005 | Hossainy et al. ............ 424/423 |
| 2005/0209548 A1 | 9/2005 | Dev |
| 2005/0215722 A1 | 9/2005 | Pinchunk et al. |
| 2005/0220853 A1 | 10/2005 | Dao et al. |
| 2005/0222677 A1 | 10/2005 | Bates et al. |
| 2005/0226991 A1 | 10/2005 | Hossainy et al. |
| 2005/0233061 A1 | 10/2005 | Schwarz |
| 2005/0244456 A1 | 11/2005 | Nilsson et al. |
| 2005/0244459 A1 | 11/2005 | DeWitt et al. |
| 2005/0246009 A1 | 11/2005 | Toner et al. |
| 2005/0251106 A1 | 11/2005 | Cervantes |
| 2005/0273049 A1 | 12/2005 | Krulevitch |
| 2005/0273075 A1 | 12/2005 | Krulevitch |
| 2005/0278021 A1 | 12/2005 | Bates et al. |
| 2005/0288629 A1 | 12/2005 | Kunis |
| 2006/0002968 A1 | 1/2006 | Stewart |
| 2006/0002973 A1 | 1/2006 | Barry |
| 2006/0013853 A1 | 1/2006 | Richard |
| 2006/0013854 A1 | 1/2006 | Strickler et al. |
| 2006/0020243 A1 | 1/2006 | Speck et al. |
| 2006/0020331 A1 | 1/2006 | Bates et al. |
| 2006/0025848 A1 | 2/2006 | Weber et al. |
| 2006/0041225 A1 | 2/2006 | Wallace |
| 2006/0057208 A1 | 3/2006 | Holzer et al. |
| 2006/0058815 A1 | 3/2006 | Mickley et al. |
| 2006/0067977 A1 | 3/2006 | Labrecque et al. |
| 2006/0079836 A1 | 4/2006 | Holman et al. |
| 2006/0083768 A1 | 4/2006 | Labrecque et al. |
| 2006/0085058 A1 | 4/2006 | Rosenethal et al. |
| 2006/0088566 A1* | 4/2006 | Parsonage et al. ............ 424/422 |
| 2006/0088596 A1 | 4/2006 | Labrecque |
| 2006/0112536 A1 | 6/2006 | Herweck et al. |
| 2006/0121081 A1 | 6/2006 | Labrecque et al. |
| 2006/0121088 A1 | 6/2006 | Hunter |
| 2006/0129093 A1 | 6/2006 | Jackson |
| 2006/0134160 A1 | 6/2006 | Troczynski et al. |
| 2006/0134168 A1 | 6/2006 | Chappa et al. |
| 2006/0135548 A1 | 6/2006 | Keri |
| 2006/0147491 A1 | 7/2006 | DeWitt et al. |
| 2006/0165754 A1 | 7/2006 | Ranade |
| 2006/0167407 A1 | 7/2006 | Weber et al. |
| 2006/0171982 A1 | 8/2006 | Timm |
| 2006/0171984 A1 | 8/2006 | Cromack et al. |
| 2006/0171985 A1 | 8/2006 | Richard et al. |
| 2006/0184112 A1 | 8/2006 | Horn |
| 2006/0190022 A1 | 8/2006 | Beyar et al. |
| 2006/0193890 A1 | 8/2006 | Owens |
| 2006/0193891 A1 | 8/2006 | Richard |
| 2006/0195176 A1 | 8/2006 | Bates et al. |
| 2006/0200048 A1 | 9/2006 | Furst |
| 2006/0200556 A1 | 9/2006 | Brave |
| 2006/0204537 A1 | 9/2006 | Ratner et al. |
| 2006/0212106 A1 | 9/2006 | Weber et al. |
| 2006/0224115 A1 | 10/2006 | Willard |
| 2006/0228452 A1 | 10/2006 | Cromack et al. |
| 2006/0240070 A1 | 10/2006 | Cromack et al. |
| 2006/0280858 A1 | 12/2006 | Kokish |
| 2006/0286071 A1 | 12/2006 | Epstein et al. |
| 2006/0286141 A1 | 12/2006 | Campbell |
| 2007/0003599 A1 | 1/2007 | Schwarz |
| 2007/0020307 A1 | 1/2007 | Zhong et al. |
| 2007/0027523 A1 | 2/2007 | Toner et al. |
| 2007/0067882 A1 | 3/2007 | Atanasoska et al. |
| 2007/0078413 A1 | 4/2007 | Stenzel |
| 2007/0083149 A1 | 4/2007 | Steward et al. |
| 2007/0088246 A1 | 4/2007 | Steward et al. |
| 2007/0088255 A1 | 4/2007 | Toner et al. |
| 2007/0093745 A1 | 4/2007 | Steward et al. |
| 2007/0104766 A1 | 5/2007 | Wang |
| 2007/0106250 A1 | 5/2007 | Seward et al. |
| 2007/0106363 A1 | 5/2007 | Weber |
| 2007/0112330 A1 | 5/2007 | Palasis |
| 2007/0129474 A1 | 6/2007 | Salamone |
| 2007/0129792 A1 | 6/2007 | Picart et al. |
| 2007/0150465 A1 | 6/2007 | Brave |
| 2007/0150466 A1 | 6/2007 | Brave |
| 2007/0150470 A1 | 6/2007 | Brave |
| 2007/0150515 A1 | 6/2007 | Brave |
| 2007/0150646 A1 | 6/2007 | Yoon |
| 2007/0154554 A1 | 7/2007 | Burgermeister et al. |
| 2007/0178136 A1* | 8/2007 | Arney et al. ................... 424/426 |
| 2007/0185561 A1 | 8/2007 | Schmitz |
| 2007/0212386 A1 | 9/2007 | Patravale et al. |
| 2007/0212387 A1 | 9/2007 | Patravale et al. |
| 2007/0212393 A1 | 9/2007 | Patravale et al. |
| 2007/0212394 A1 | 9/2007 | Reyes et al. |
| 2007/0224234 A1 | 9/2007 | Steckel et al. |
| 2007/0225800 A1 | 9/2007 | Sahatjian et al. |
| 2007/0232996 A1 | 10/2007 | Andersen |
| 2007/0244548 A1 | 10/2007 | Myers et al. |
| 2007/0244549 A1 | 10/2007 | Pathak |
| 2007/0254010 A1 | 11/2007 | Richard |
| 2007/0255206 A1 | 11/2007 | Reneker |
| 2007/0292478 A1 | 12/2007 | Youri |
| 2008/0020013 A1 | 1/2008 | Reyes et al. |
| 2008/0021385 A1 | 1/2008 | Barry et al. |
| 2008/0027421 A1 | 1/2008 | Vancelette |
| 2008/0031173 A1 | 2/2008 | Zhang |
| 2008/0040314 A1 | 2/2008 | Brave |
| 2008/0050415 A1 | 2/2008 | Atanasoska et al. |
| 2008/0051541 A1 | 2/2008 | Strickler et al. |
| 2008/0057102 A1 | 3/2008 | Roorda |
| 2008/0071350 A1 | 3/2008 | Stinson |
| 2008/0071358 A1 | 3/2008 | Weber |
| 2008/0089958 A1 | 4/2008 | Diehl |
| 2008/0091008 A1 | 4/2008 | Viswanath |
| 2008/0095847 A1 | 4/2008 | Glauser et al. |
| 2008/0102033 A1 | 5/2008 | Speck et al. |
| 2008/0102034 A1 | 5/2008 | Speck et al. |
| 2008/0104004 A1 | 5/2008 | Brave |
| 2008/0113081 A1 | 5/2008 | Hossainy et al. |
| 2008/0114331 A1 | 5/2008 | Holman |
| 2008/0118544 A1 | 5/2008 | Wang |
| 2008/0132992 A1 | 6/2008 | Bates et al. |
| 2008/0140002 A1 | 6/2008 | Ramzipoor et al. |
| 2008/0145396 A1 | 6/2008 | Bates et al. |
| 2008/0145398 A1 | 6/2008 | Bates et al. |
| 2008/0157444 A1 | 7/2008 | Melsheimer |
| 2008/0171129 A1 | 7/2008 | Ranade et al. |
| 2008/0175887 A1 | 7/2008 | Wang |
| 2008/0195042 A1 | 8/2008 | Weber |
| 2008/0195079 A1 | 8/2008 | Moore et al. |
| 2008/0199506 A1 | 8/2008 | Horres |
| 2008/0206304 A1 | 8/2008 | Lindquist et al. |
| 2008/0208182 A1 | 8/2008 | Lafontaine |
| 2008/0220041 A1 | 9/2008 | Brito et al. |
| 2008/0249464 A1 | 10/2008 | Spencer et al. |
| 2008/0255508 A1 | 10/2008 | Wang |
| 2008/0255509 A1 | 10/2008 | Wang |
| 2008/0255510 A1 | 10/2008 | Wang |
| 2008/0274159 A1 | 11/2008 | Schultz |
| 2008/0276935 A1 | 11/2008 | Wang |
| 2008/0287984 A1 | 11/2008 | Weber et al. |
| 2008/0311173 A1 | 12/2008 | Schwarz et al. |
| 2009/0005849 A1 | 1/2009 | Hossainy et al. |
| 2009/0018501 A1 | 1/2009 | Yribarren et al. |
| 2009/0024200 A1 | 1/2009 | Wilcox et al. |
| 2009/0047414 A1 | 2/2009 | Corbeil et al. |
| 2009/0048667 A1 | 2/2009 | Mochizuki |
| 2009/0054837 A1 | 2/2009 | Won Holst et al. |
| 2009/0069883 A1 | 3/2009 | Ding et al. |
| 2009/0076448 A1 | 3/2009 | Consigny et al. |
| 2009/0088735 A1 | 4/2009 | Abboud |
| 2009/0098176 A1 | 4/2009 | Helmus |

(56) References Cited

U.S. PATENT DOCUMENTS

| | | |
|---|---|---|
| 2009/0105686 A1 | 4/2009 | Snow et al. |
| 2009/0105687 A1 | 4/2009 | Deckman et al. |
| 2009/0111960 A1 | 4/2009 | Parsonage |
| 2009/0112239 A1 | 4/2009 | To |
| 2009/0120361 A1 | 5/2009 | Schiele |
| 2009/0136560 A1 | 5/2009 | Bates et al. |
| 2009/0187144 A1 | 7/2009 | Jayaraman |
| 2009/0192537 A1 | 7/2009 | Obrien |
| 2009/0204082 A1 | 8/2009 | Wesselmann et al. |
| 2009/0226502 A1 | 9/2009 | Chen |
| 2009/0227948 A1 | 9/2009 | Chen et al. |
| 2009/0227949 A1 | 9/2009 | Knapp et al. |
| 2009/0227980 A1 | 9/2009 | Kangas et al. |
| 2009/0246252 A1 | 10/2009 | Arps et al. |
| 2009/0254063 A1 | 10/2009 | Oepen et al. |
| 2009/0258049 A1 | 10/2009 | Klein et al. |
| 2009/0276036 A1 | 11/2009 | Nagura |
| 2009/0299355 A1 | 12/2009 | Bencini |
| 2009/0299356 A1 | 12/2009 | Watson |
| 2009/0318848 A1 | 12/2009 | Shippy, III et al. |
| 2010/0010470 A1 | 1/2010 | Bates |
| 2010/0015200 A1 | 1/2010 | McClain et al. |
| 2010/0023108 A1 | 1/2010 | Toner et al. |
| 2010/0030183 A1 | 2/2010 | Toner et al. |
| 2010/0036585 A1 | 2/2010 | Scharfenberg |
| 2010/0049294 A1 | 2/2010 | Zukowski et al. |
| 2010/0049296 A1 | 2/2010 | Sarasam et al. |
| 2010/0049309 A1 | 2/2010 | Bates et al. |
| 2010/0055294 A1 | 3/2010 | Wang et al. |
| 2010/0056985 A1 | 3/2010 | Weber et al. |
| 2010/0063585 A1 | 3/2010 | Hoffmann et al. |
| 2010/0069838 A1 | 3/2010 | Weber |
| 2010/0074934 A1 | 3/2010 | Hunter |
| 2010/0076542 A1 | 3/2010 | Orlowski |
| 2010/0087783 A1 | 4/2010 | Weber et al. |
| 2010/0092540 A1 | 4/2010 | Pinchuk et al. |
| 2010/0096781 A1 | 4/2010 | Huang et al. |
| 2010/0125239 A1 | 5/2010 | Perry et al. |
| 2010/0131043 A1 | 5/2010 | Casas et al. |
| 2010/0145266 A1 | 6/2010 | Orlowski |
| 2010/0179475 A1 | 7/2010 | Hoffmann et al. |
| 2010/0198190 A1 | 8/2010 | Michal et al. |
| 2010/0209471 A1 | 8/2010 | Weber |
| 2010/0209473 A1 | 8/2010 | Dhont et al. |
| 2010/0228333 A1 | 9/2010 | Drasler et al. |
| 2010/0233228 A1 | 9/2010 | Speck |
| 2010/0233236 A1 | 9/2010 | Zhao |
| 2010/0239635 A1 | 9/2010 | McClain |
| 2010/0249702 A1 | 9/2010 | Magana et al. |
| 2010/0256748 A1 | 10/2010 | Taylor |
| 2010/0261662 A1 | 10/2010 | Schreck et al. |
| 2010/0268191 A1 | 10/2010 | Trudel et al. |
| 2010/0272773 A1 | 10/2010 | Kangas et al. |
| 2010/0272778 A1 | 10/2010 | McClain |
| 2010/0285085 A1 | 11/2010 | Stankus et al. |
| 2010/0292641 A1 | 11/2010 | Wijay et al. |
| 2010/0298769 A1 | 11/2010 | Schewe et al. |
| 2010/0312182 A1 | 12/2010 | Adden et al. |
| 2010/0318020 A1 | 12/2010 | Atanasoska et al. |
| 2010/0324645 A1 | 12/2010 | Stankus et al. |
| 2010/0324648 A1 | 12/2010 | Scheller et al. |
| 2010/0331816 A1 | 12/2010 | Dadino et al. |
| 2010/0331947 A1 | 12/2010 | Shalev et al. |
| 2011/0008260 A1 | 1/2011 | Flanagan |
| 2011/0015664 A1 | 1/2011 | Kangas |
| 2011/0020151 A1 | 1/2011 | Tiefenthaler |
| 2011/0054396 A1 | 3/2011 | Kangas et al. |
| 2011/0054443 A1 | 3/2011 | Weber |
| 2011/0087191 A1 | 4/2011 | Scheuermann |
| 2011/0152765 A1 | 6/2011 | Weber |
| 2011/0160645 A1 | 6/2011 | Sutermeister |
| 2011/0160659 A1 | 6/2011 | Clarke |
| 2011/0160698 A1 | 6/2011 | Hoffmann |
| 2011/0178503 A1 | 7/2011 | Kangas |
| 2011/0196340 A1 | 8/2011 | Barry |
| 2011/0251590 A1 | 10/2011 | Weber |
| 2011/0270152 A1 | 11/2011 | Atanasoska |
| 2011/0275980 A1 | 11/2011 | Weber |
| 2011/0301565 A1 | 12/2011 | Weber |
| 2012/0059316 A1 | 3/2012 | Owens |
| 2012/0078227 A1 | 3/2012 | Kangas |
| 2012/0231037 A1 | 9/2012 | Levi |
| 2013/0035483 A1 | 2/2013 | Zeng |
| 2013/0053947 A1 | 2/2013 | Kangas |

FOREIGN PATENT DOCUMENTS

| | | |
|---|---|---|
| DE | 102004020856 | 4/2005 |
| EP | 0383429 | 1/1990 |
| EP | 0372088 | 6/1990 |
| EP | 0379156 | 7/1990 |
| EP | 0399712 | 11/1990 |
| EP | 0470246 | 2/1991 |
| EP | 0551182 | 7/1993 |
| EP | 0568310 | 11/1993 |
| EP | 0734721 | 3/1996 |
| EP | 0747069 | 4/1996 |
| EP | 0519063 | 5/1996 |
| EP | 0712615 | 5/1996 |
| EP | 0717041 | 6/1996 |
| EP | 0770401 | 5/1997 |
| EP | 0633796 | 11/1997 |
| EP | 0937469 | 8/1999 |
| EP | 0950386 | 10/1999 |
| EP | 2241341 | 1/2001 |
| EP | 0623354 | 10/2002 |
| EP | 1189553 | 3/2004 |
| EP | 1407726 | 4/2004 |
| EP | 1521603 | 4/2005 |
| EP | 1667760 | 6/2006 |
| EP | 1372737 | 12/2006 |
| EP | 1810665 | 7/2007 |
| EP | 1666071 | 8/2007 |
| EP | 1666070 | 9/2007 |
| EP | 1857127 | 11/2007 |
| EP | 1539266 | 4/2008 |
| EP | 1981559 | 10/2008 |
| EP | 1996246 | 12/2008 |
| EP | 2043704 | 4/2009 |
| EP | 2108390 | 10/2009 |
| EP | 2125058 | 12/2009 |
| EP | 2125060 | 12/2009 |
| EP | 1594459 | 2/2010 |
| EP | 1669092 | 3/2010 |
| EP | 2172242 | 4/2010 |
| EP | 1534356 | 7/2010 |
| EP | 1786487 | 11/2010 |
| EP | 2251050 | 11/2010 |
| GB | 2112646 | 7/1983 |
| GB | 2127839 | 9/1983 |
| JP | 663145 | 3/1994 |
| JP | 663145 A | 3/1994 |
| JP | 2002240847 | 8/2002 |
| RU | 200513564 | 4/2004 |
| WO | 1989012478 | 12/1989 |
| WO | 1991008790 | 6/1991 |
| WO | 1992011896 | 7/1992 |
| WO | 1992015286 | 9/1992 |
| WO | 1993006792 | 4/1993 |
| WO | 1994021308 | 9/1994 |
| WO | 1994023787 | 10/1994 |
| WO | 9503036 | 2/1995 |
| WO | 9503083 | 2/1995 |
| WO | 1995003036 | 2/1995 |
| WO | 1995008305 | 3/1995 |
| WO | 1995021636 | 8/1995 |
| WO | 1996025176 | 8/1996 |
| WO | 1996032907 | 10/1996 |
| WO | 9639949 | 12/1996 |
| WO | 1997010011 | 3/1997 |
| WO | 1997025085 | 7/1997 |
| WO | 9733552 | 9/1997 |
| WO | 9741916 | 11/1997 |
| WO | 1998031415 | 7/1998 |

(56) References Cited

FOREIGN PATENT DOCUMENTS

| | | |
|---|---|---|
| WO | 9901458 | 1/1999 |
| WO | 9908729 | 2/1999 |
| WO | 1999008729 | 2/1999 |
| WO | 99/16500 | 4/1999 |
| WO | 99/25336 | 5/1999 |
| WO | 1999029353 | 6/1999 |
| WO | 00/32267 | 6/2000 |
| WO | 0032238 | 6/2000 |
| WO | 0032238 A1 | 6/2000 |
| WO | 2000032238 | 6/2000 |
| WO | 00/45744 | 8/2000 |
| WO | 2000/062830 | 10/2000 |
| WO | 0149358 | 7/2001 |
| WO | 0160441 | 8/2001 |
| WO | 0238065 | 5/2002 |
| WO | 2002043796 | 6/2002 |
| WO | 2002/087651 | 7/2002 |
| WO | 02076509 | 10/2002 |
| WO | 03022265 | 3/2003 |
| WO | 2003026718 | 4/2003 |
| WO | 2003/039612 | 5/2003 |
| WO | 2003059430 | 7/2003 |
| WO | 03094991 | 11/2003 |
| WO | 2004028582 | 4/2004 |
| WO | 2004028610 | 4/2004 |
| WO | 2004050140 | 6/2004 |
| WO | 2004060346 | 7/2004 |
| WO | 2004060471 | 7/2004 |
| WO | 2004089958 | 10/2004 |
| WO | 2004091684 | 10/2004 |
| WO | 2005027994 | 3/2005 |
| WO | 2005027996 | 3/2005 |
| WO | 2005032611 | 4/2005 |
| WO | 2005/082434 | 9/2005 |
| WO | 2006036970 | 4/2006 |
| WO | 2006039237 | 4/2006 |
| WO | 2006/102359 | 9/2006 |
| WO | 2006108420 | 10/2006 |
| WO | 2006116348 | 11/2006 |
| WO | 2006116989 | 11/2006 |
| WO | 2006130326 | 12/2006 |
| WO | 2007011707 | 1/2007 |
| WO | 2007090382 | 8/2007 |
| WO | 2007090385 | 8/2007 |
| WO | 2007106441 | 9/2007 |
| WO | 2008/003298 | 1/2008 |
| WO | 2008014222 | 1/2008 |
| WO | 2008045228 | 4/2008 |
| WO | 2008/086794 | 7/2008 |
| WO | 2008/089730 | 7/2008 |
| WO | 2008101486 | 8/2008 |
| WO | 2007109114 | 9/2008 |
| WO | 2008109114 | 9/2008 |
| WO | 2008/125890 | 10/2008 |
| WO | 2008/137237 | 11/2008 |
| WO | 2009002855 | 12/2008 |
| WO | 2009014692 | 1/2009 |
| WO | 2009018816 | 2/2009 |
| WO | 2009/036118 | 3/2009 |
| WO | 2009026914 | 3/2009 |
| WO | 2009036135 | 3/2009 |
| WO | 2009/066330 | 5/2009 |
| WO | 2009096822 | 8/2009 |
| WO | 2009100394 | 8/2009 |
| WO | 2009120361 | 10/2009 |
| WO | 2009121565 | 10/2009 |
| WO | 2009/135125 | 11/2009 |
| WO | 2010009335 | 1/2010 |
| WO | 2010/021757 | 2/2010 |
| WO | 2010026578 | 3/2010 |
| WO | 2010079218 | 7/2010 |
| WO | 2010080575 | 7/2010 |
| WO | 2010086863 | 8/2010 |
| WO | 2010096476 | 8/2010 |
| WO | 2010111232 | 9/2010 |
| WO | 2010120620 | 10/2010 |
| WO | 2010124098 | 10/2010 |
| WO | 2010124098 A2 | 10/2010 |
| WO | 2010147805 | 12/2010 |
| WO | 2011005421 A2 | 1/2011 |
| WO | 2011009096 | 1/2011 |
| WO | 2011028419 | 3/2011 |

OTHER PUBLICATIONS

Abstract from Liggins, R. T., Hunter, W. L and Burt, H. M. 'Solid-state characterization of paclitaxel.' Journal of Pharmaceutical Sciences, 86: 1458-1463, (1997).

Abstracts from the 70th Scientific Sessions, Orange County Convention center, Orlando, Florida, Nov. 9-12, 1997, Supplement to Circulation, vol. 96, No. 8, Supplement I, 1-341,1-288 and 1-608.

Alexis et al., 'In vitro study of release mechanisms of paclitaxel and rapamycin from drug-incorporated biodegradable stent matrices' Journal of Controlled Release 98 (2004) 67-74.

Axel, Dorothea I., et al., Paclitaxel Inhibits Arterial Smooth Muscle Cell Proliferation and Migration In Vitro and In Vivo Using Local Drug Delivery, Jul. 15, 1997, vol. 96 (2), 636-651.

Axel De Labriolle et al., "Paclitaxel-eluting balloon: From bench to bed", Catheterization and Cardiovascular Interventions, vol. 73. No. 5, Apr. 1, 2009, pp. 643-652.

Buvardi, S., et al., 'Merck Index', 1996, Merck and Co., p. 144.

Cardiovascular and Interventional Radiology, Supplement 1, Sep. 28-Oct. 2, 1997, 158-161.

Consigny PM, Barry JJ, Vitali NJ.; 'Local Delivery of an Antiproliferative Drug with Use of Hydrogel-coated Angioplasty Balloons1' J Vasc Intery Radiol. Jul.-Aug. 1994;5(4):553-60.

Cortese et al., "Paclitaxel-coated balloon versus drug-eluting stent during PCI of small coronary vessels, a prospective randomised clinical trial. The PICCOLETO Study", Heart 2010; 96:1291-1296.

Finkelstein et al., "Local Drug Delivery via a Coronary Stent with Programmable Release Pharmocokinetics," 2003, Circulation, 107, 777-784.

International Preliminary Report on Patentability of International Application No. PCT/DE20071001173 dated Aug. 4, 2009.

J. Wohrle et al., 'Comparison of the heparin coated vs the uncoated Jostent no nfluence on restenosis or clinical outcome' European Heart Journal, 2001, vol. 22, pp. 1808-1816.

Partial European Search Report in EP 07005256.8, dated Jan. 25, 2008.

PCT/US 08/72660 Search Report, dated Nov. 6, 2008.

PCT/US 2005/47235 Search Report, dated Dec. 28, 2005.

Presentation by Dr. Cortese, "Paclitaxel-eluting balloon versus paclitaxel-eluting stent in small coronary vessel disease." The Piccoleto Trial.

U.S. Appl. No. 61/322,451, filed Apr. 9, 2010.
U.S. Appl. No. 61/330,201, filed Apr. 30, 2010.
U.S. Appl. No. 61/332,544, filed Apr. 9, 2010.
U.S. Appl. No. 61/352,117, filed Jun. 7, 2010.
U.S. Appl. No. 61/379,608, filed Sep. 2, 2010.
U.S. Appl. No. 61/385,849, filed Sep. 23, 2010.
U.S. Appl. No. 61/394,104, filed Oct. 18, 2010.
U.S. Appl. No. 61/421,054, filed Dec. 8, 2010.

Scheller et al., "Treatment of Coronary In-Stent Restenosis with a Paclitaxel-Coated Balloon Catheter", The New England Journal of Medicine, 2006; 355:2113-24.

Scollott, S.J., et al., Taxol Inhibits Neointimal Smooth Muscle Cell Accumulation after Angioplasty in the Rat, 1995, Journal of Clinical Investigation, 95, pp. 1869-1876.

Westedt et al., "Paclitaxel releasing films consisting of poly(vinyl alcohol)-graft-poly(lactide-co-glycolide) and their potential as biodegradable stent coatings." 2006, J Control Release 111, 235-46 (abstract).

Written Opinion for PCT/DE2008/000096.

Xu et al., "Lactic-co-glycolic acid polymer with rapamycin coated stent reduces neo-intimal formation in a porcine coronary model", Journal of Clinical Cardiology, 2004, abstract.

Dowding et al., "Preparation and Swelling Properties of Poly(NIPAM) "Minigel" Particles Prepared by Inverse Suspension Polymerization," Journal of Colloid and Interface Science 221, 268-272 (2000).

(56) References Cited

OTHER PUBLICATIONS

Panda et al., "Synthesis and swelling characteristics of poly(N-isopropylacrylamide) temperature sensitive hydrogels crosslinked by electron beam irradiation," Radiation Physics and Chemistry 58 (2000) 101-110.
U.S. Appl. No. 61/394,104, filed Oct. 18, 2010; Inventor: Radhakrishnan et al.
Scheller et al., "A further alternative; Balloons can be coated, as well" Newsletter from annual meeting in DGK Apr. 21, 2006.
R. Charles, et al, "Ceramide-Coated Balloon Catheters Limit Neointimal Hyperplasia After Stretch Injury in Cartoid Arteries," Circ. Res. 2000;87;282-288.
D. Mastropaolo, et al, "Crystal and molecular structure of paclitaxel (taxol)," Proc. Natl. Acad. Sci. USA, 92, pp. 6920-6924 (Jul. 1995).
Sigma-Aldrich, "Paclitaxel" Product Information, date unknown. Documents indicates 06/09 in lower corner. Applicant does not know if this is a date.
Mondesire (Targeting Mammalian Target of Rapamycin Synergistically Enhances Chemotherapy-Induced Cytotoxicity in Breast Cancer Cells, 10 Clin. Cancer Res. 7031 (2004).
U.S. Appl. No. 61/515,500, filed Aug. 5, 2011.
U.S. Appl. No. 61/271,167, filed Jul. 17, 2009.
U.S. Appl. No. 61/527,203, filed Aug. 25, 2011.
Minghetti P et al: "Sculptured drug-eluting stent for the on-site delivery of tacrolimus", European Journal of Pharmaceutics and Biopharmaceutics E Lsevier Science Publishers B.V. Amsterdam. NL v No. 73 No. 3 Nov. 1, 2009 (Nov. 1, 2009) pp. 331-336 is cited herein.
U.S. Appl. No. 61/224,723, filed Jul. 10, 2009.
U.S. Appl. No. 61/172,629, filed Apr. 24, 2009.
PCT Search Report and Written Opinion for PCT/US2010/038532.
Westedt, et al., Paclitaxel releasing films consisting of poly(vinyl alcohol)-graft-poly-(lactide-co-glycolide) and their potential as biodegradable stent coatings, Journal of Controlled Release, 2006, 111, 235-246. Epub Feb. 8, 2006.

\* cited by examiner

NUCLEATION OF DRUG DELIVERY BALLOONS TO PROVIDE IMPROVED CRYSTAL SIZE AND DENSITY

CROSS-REFERENCE TO RELATED APPLICATIONS

This application claims the benefit of Application No. 61/271,167, filed Jul. 17, 2009, the entire contents of which is hereby incorporated by reference.

BACKGROUND OF THE INVENTION

Balloons coated with paclitaxel containing formulations are known. In some cases paclitaxel has been applied directly to the balloon or to a coating placed on the balloon. In other cases paclitaxel has been formulated with an excipient that may be polymer, a contrast agent, a surface active agent, or other small molecules that facilitate adhesion to the balloon and/or release from the balloon upon expansion. The formulations have typically been applied from solution, and may be applied to the entire balloon or to a folded balloon, either by spraying, immersion or by pipette along the fold lines.

Paclitaxel coated balloons that provide high release rates from the balloon surface have recently been developed. However these balloons do not yet provide for delivery of predictable amounts of the drug to the tissue at the delivery site nor do they provide for a predictable therapeutic drug tissue level over an extended time period.

Earlier investigations of paclitaxel coated balloons by the applicant have shown that it is desirable to control the morphology of the drug on the balloon, that dihhydrate paclitaxel crystalline form facilitates longer tissue residence time, and that the formation of crystalline paclitaxel dihydrate can be controlled by use of vapor annealing of the balloon. U.S. application 61/172,629 filed Apr. 24, 2009 describes this work in more detail and is incorporated herein by reference in its entirety.

SUMMARY OF THE INVENTION

When forming a crystalline drug on a balloon it has been found that the conditions of deposition of the drug on the balloon can be influenced to produce drug crystals on a balloon of high density and small size that provide improved delivery characteristics.

In one aspect the invention describes a method of forming a drug delivery balloon that provides nucleation sites on the balloon to control the crystalline particle size of paclitaxel or another drug. Control of particle size influence transfer and dissolution of the drug. Other aspects of the invention relation to balloons that may be produced by such methods.

In some embodiments the invention pertains to a method of making a drug delivery balloon having a coating thereon comprising a drug, wherein the drug has characteristic amorphous and crystalline forms comprising:
 a) applying a coating of the drug in amorphous form, and
 b) annealing the coated balloon to produce a crystalline form of the drug in situ on the balloon,
wherein in the applying step a) the drug coating is applied to a balloon surface that has been nucleated to induce formation of drug crystals in the annealing step. Various techniques of nucleating the balloon are described, including particular embodiments involving vapor pretreatment of the balloon to induce blooming of a component of the balloon material as a nucleating agent.

In other embodiments the invention pertains to a drug delivery balloon comprising a layer of crystalline drug particles of average length less than 100 μm length substantially uniformly distributed over the balloon; or to a drug delivery balloon comprising a layer of crystalline drug particles of less than 100 μm average length densely packed on at least a portion of the surface of the balloon.

Still other aspects of the invention are described in the Figures, the Detailed Description of Preferred Embodiments and/or in the Claims below.

BRIEF DESCRIPTION OF THE FIGURES

FIG. 3b is a higher resolution image of a coating similar to FIG. 3a.

FIG. 5b is surface region of a balloon as in FIG. 5a.

DETAILED DESCRIPTION OF PREFERRED EMBODIMENTS

Figure 1:
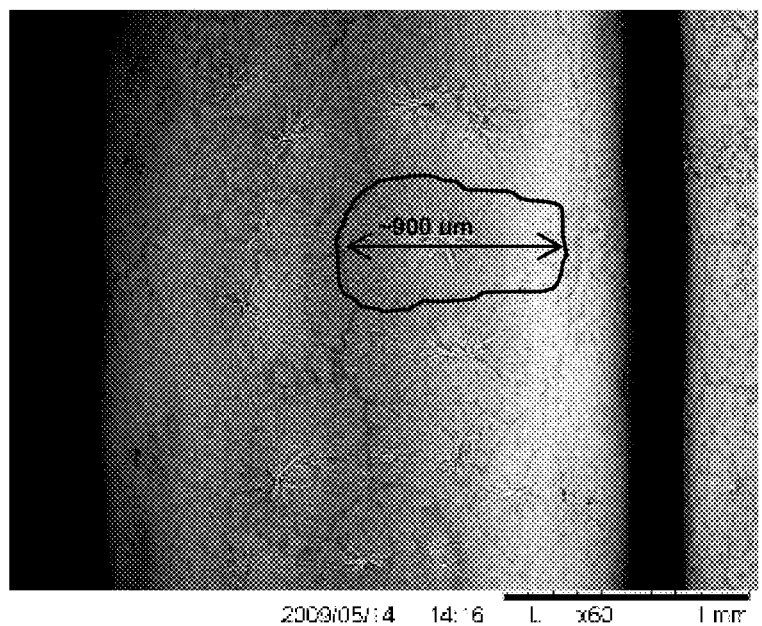
FIG. 1 is a magnified image showing crystal size of paclitaxel/PVP coated on an untreated balloon and crystallized by vapor annealing.

Drugs such as paclitaxel ("Ptx") are suitably delivered from a drug delivery balloon in a crystalline form, or substantially in crystalline form in order to maximize tissue residence time at the delivery site. The coating however must be sufficiently coherent to allow for tracking to the treatment site and yet readily loose adherence to the balloon upon expansion of the balloon. In the flowing system it is also desirable that delivery to the tissue site be maximized, systemic loss (non-localized delivery) be minimized and that the material lost systemically have minimal size for safety reasons. In particular it is desirable to minimize particle size to reduce the risk of particles lost from the coated balloon lodging in the patient's vascular capillary system. Further, the size, distribution and crystallinity of the drug particles play a critical role in tissue uptake and duration. Methods to control these factors are important in designing drug delivery balloons.

According to some embodiments of the invention the drug is one that has crystalline and amorphous forms, and is desirably delivered in a crystal form. The drugs which can be used in embodiments of the present invention, can be any therapeutic agent or substance that has therapeutic benefit for local administration by delivery from a medical device inserted into the body and that also exists in such polymorph forms. In this aspect the drug is coated on the balloon, with or without an excipient, in an amorphous form and then is converted to the desired crystalline form in an annealing step that grows the crystalline drug in the coating in-situ on the balloon. This gives a packed system of crystals on the surface that more closely approximate the desired properties of a drug delivery balloon.

In some embodiments the drug is a lipophilic substantially water insoluble drug, such as paclitaxel or another drug that inhibits restenosis, for instance paclitaxel analogous and derivatives, rapamycin rapamycin analogous and derivatives, everolimus, everolimus analogous and derivatives, and mixtures thereof. Other drugs that may be suitable are described in documents identified later herein. Mixtures of drugs, for instance paclitaxel and rapamycin, or their analogs or derivatives may be employed. The drug is suitably one that is able to form a crystalline form by treatment with a solvent or solvent vapor after it is applied to the balloon.

Some embodiments further involve applying the amorphous drug coating to a balloon that has been nucleated to induce crystallization during the annealing step. Nucleation of the balloon may be provided by providing the balloon surface with a specific texturization, by pretreating the balloon with a nucleating agent effective for inducing crystallization of the specific drug, by inducing migration to the balloon surface (blooming) of a component of the balloon substrate that functions as a nucleating agent, or by utilizing a material for the drug delivery balloon for which such blooming occurs intrinsically under the processing conditions of balloon formation, aging or drug coating processing.

In some embodiments the drug is formulated with an excipient. An excipient is an additive to a drug-containing layer that facilitates adhesion to the balloon and/or release from the balloon upon expansion. The excipient may be polymer, a contrast agent, a surface active agent, or other small molecule. In at least some embodiments the drug is substantially insoluble in the excipient.

In some embodiments the excipient may remain on the delivery device at the time of drug transfer but allow efficient transfer of the drug from the mixture. In some embodiments the excipient provides weak phase boundaries with the drug particles that are easily overcome when a balloon is expanded, regardless of whether the excipient remains on the device or initially leaves the device with the drug. In some embodiments the excipient substantially degrades or dissolves in the course of the deployment or during transfer of the drug from the device at the site of administration such that little or none of the excipient is detectable on the tissue after a short interval, for instance an interval of 2 days, 1 day, 12 hours, 4 hours, 1 hour, 30 minutes, 10 minutes or 1 minute. In some embodiments dissolution or degradation of the excipient during deployment provides porosities in the drug-containing layer by the time the device is at the site of administration.

Examples of excipients that may be employed include polymeric and non-polymeric additive compounds, including polyvinylpyrrolidone (PVP), sugars such as mannitol, contrast agents such as iopromide, citrate esters such as acetyltributyl citrate, glycerol esters of short chain (i.e. $C_2$-$C_8$) mono-carboxylic acids such as triacetin, and pharmaceutically acceptable salts.

In some embodiments the drug is applied to a device, such as a balloon, that provides transient contact delivery of the drug directly to tissue, without use of a release regulating polymer such as is typically present on drug eluting stents or in microencapsulated drug particles.

In some embodiments the drug may be coated with a protective polymeric layer that functions to reduce loss during deployment of the device to the site of administration, but that substantially disintegrates in the course of the deployment or during transfer of the drug from the device at the site of administration. Suitably such protective layer has a thickness of 0.5 µm or less, 0.1 µm or less, or 0.01 µm or less. Polymers or copolymers that have a good solubility in water and a molecular weight sufficient to slow dissolution of the coating enough to provide practical protection may be used. Other protective layers may be effective if they break up into fine particles during drug delivery, for instance upon balloon expansion. Protective coating thickness may be adjusted to give an acceptable dissolution and/or degradation profile.

In some embodiments the drug containing layer is applied over an underlayer of material that has a high solubility in bodily fluids to undercut the drug facilitate breakup of the drug-containing layer upon balloon expansion. An example of a suitable underlayer material is pectin.

Numerous other excipients and additive compounds, protective polymer layers, underlayer materials and drugs are described in one or more of the following documents:
U.S. Pat. No. 5,102,402, Dror et al (Medtronic, Inc.)
U.S. Pat. No. 5,370,614, Amundson et al, (Medtronic, Inc.)
U.S. Pat. No. 5,954,706, Sahatjian (Boston Scientific Corp)
WO 00/32267, SciMed Life Systems; St Elizabeth's Medical Center (Palasis et al)
WO 00/45744, SciMed Life Systems (Yang et al)
R. Charles, et al, "Ceramide-Coated Balloon Catheters Limit Neointimal Hyperplasia After Stretch Injury in Cartoid Arteries," *Circ. Res.* 2000; 87; 282-288
U.S. Pat. No. 6,306,166, Barry et al, (SciMed Life Systems, Inc.)
US 2004/0073284, Bates et al (Cook, Inc; MED Inst, Inc.)
US 2006/0020243, Speck
WO 2008/003298 Hemoteq AG, (Hoffman et al)
WO 2008/086794 Hemoteq AG, (Hoffman et al)
US 2008/0118544, Wang
US 20080255509, Wang (Lutonix)
US 20080255510, Wang (Lutonix)
All incorporated herein by reference in their entirety.

According to an embodiment the invention the drug is provided on the device in a manner that is controlled to produce a predetermined ratio of said morphological forms.

In some cases of drug delivery balloons described previously, paclitaxel has been applied directly to the balloon or to a coating placed on the balloon. In other cases paclitaxel has been formulated with an excipient that may be polymer, a contrast agent, a surface active agent, or other small molecules that facilitate adhesion to the balloon and/or release from the balloon upon expansion. The formulations have typically been applied from solution, and may be applied to the entire balloon or to a folded balloon, either by spraying, immersion or by pipette along the fold lines.

It has been found that subjecting some polyamide block copolymer balloons (e.g. balloons made of Pebax® polymers such as Pebax® 6333, 7033, 7233), to ethanol vapor causes lauryl lactam (residual monomer, dimers and trimers) present in Pebax® polymer) to crystallize at the surface of the balloon. This is shown in FIGS. *6a-6c* described below. The lauryl lactam can be seen as small rod-like crystals in FIG. *6b* and square crystals observed at longer annealing times (FIG. 6c). It has been discovered that the lauryl lactam crystals can act as a nucleating agent for paclitaxel crystallization. The presence of lauryl lactam crystals provide nucleation sites and thus increased number and hence smaller crystals. The number and size of the crystals can be controlled by controlling the pre-vapor annealing time.

Taking advantage of the built-in nucleation agent present in Pebax® polymers provides a convenient way of controlling paclitaxel crystal size but the invention is not limited to lauryl lactam as nucleating agent. Other nucleating agents could be used. For example crystalline nucleating agents (particles) could be added to the dip-coating solution or applied in a pre-coat. In this way one could precisely control the concentration of nucleating agent. Potential nucleating agents are organic or inorganic crystalline water soluble compounds that already find use as drug excipients such as sodium carbonate, sodium citrate, sodium chloride, sugars, etc, that have low solubility in the solvent used to apply the drug coating. For a lipophilic drug such as paclitaxel suitable nucleating agents are likely organic compounds. In some embodiments the nucleating agent is a compound listed on the FDA database of inactive ingredients. The nucleating agent compounds are desirably insoluble in the dip-coating solvents so that they survive the drug application step in particulate form and thus can be coated as particulates at very low concentrations (ng to μg). Water soluble compounds are desirable so that upon deployment of the balloon, they would dissolve in the blood.

In some embodiments the particulate nucleating agent, whether added to the surface or produced by blooming, or otherwise is provided on the substrate, before application of the drug coating at a density of from about 10 particle/mm$^2$ to about 5000 particles/mm$^2$, or from about 100 particles/mm$^2$ to about 2000 particles/mm$^2$. The size of the particulate nucleating agent may vary. In some embodiments the particulate nucleating agent has its major dimension in the size range of from about 10 nm to about 20 μm, or from about 100 nm to about 10 μm.

Another potential method to create nucleation sites is to texture the balloon surface with micrometer (μm) or nanometer (nm) scale features that may act as nucleation sites. It is known in the field of organic chemistry that in purification of organic compounds via crystallization from solution that using a glass vessel that has scratches on the interior walls can act as nucleation sites for crystallization. The balloon surface could be textured in a number of ways such as using a textured balloon mold or by texturing via laser.

In some embodiments, the rate at which the solvent evaporates within the chamber and the time in which the balloon resides in the container may be important to durablility of the drug coating microstructure. For example when an amount of solvent is added to the base of the a vapor annealing chamber in a small Petri dish and the balloon catheter is held in the chamber for 4 hours the coating has been observed to have improved durability to resist delamination while being manipulated in subsequent folding and balloon protector application steps compared to balloons that were added to the annealing chamber after it has first been saturated ethanol vapor from a larger surface to volume source that resulted from covering the bottom of the annealing chamber with ethanol. In some embodiments the volume to surface ratio (ml/cm$^2$) may be about 35-about 75 for instance about 45-55.

Vapor annealing time for forming the crystalline drug on the balloon may range widely, for instance from about 5 minutes to about 24 hours, or even longer. A typical time may be at least 30 minutes up to about 16 hours. The solvent suitably is one that induces crystallization of the drug without attacking the balloon. In some embodiments an alcohol solvent is employed, for instance a $C_1$-$C_4$ alcohol.

After the vapor annealing step the balloon catheter may be dried in a vacuum oven or by exposure to ambient conditions. In some embodiments a vacuum drying step may also contribute to improvement of coating durability as compared to ambient drying conditions.

The following non-limiting examples illustrate aspects of the invention and of the prior art.

Example 1. Dip Coat and Anneal Processes (a) Fan-Like Crystal Morphology

A 20% solution of paclitaxel/PVP (55K MW) (95/5 wt/wt) in 95/5 (wt/wt) THF/IPA is prepared. A Quantum Maverick balloon (3.0 mm dia.×16 mm length, Pebax® 7233) is coated in the inflated condition by dipping into the paclitaxel solution, removing and drying under vacuum at room temp to give a dry coat wt of about 450 ug. The coating at this point is an amorphous glass. The balloon catheter is placed in a 9 liter glass chamber. The chamber is charged with 16 g of 190 proof ethanol. The surface area of the ethanol in the bottom of the chamber is 176 cm$^2$. The catheter is suspended above the ethanol (not in contact with the liquid ethanol). The chamber is then sealed and the vapor annealing process is allowed to proceed for 4-16 hr at room temperature to cause crystallization of paclitaxel. The crystalline form of the drug is paclitaxel dihydrate.

The crystals are fan-like, apparently spherulite, crystals of large size (>100 μm, typically 200-1000 μm diameter). FIG. 1 is exemplary.

(b) Small Rod-Like Crystalline Morphology

An uncoated Quantum Maverick balloon (3.0 mm dia.×16 mm length) is placed in a sealed chamber containing saturated ethanol vapor overnight. The balloon is then dip coated as described above (a). The coating at this point is an amorphous glass. The coated balloon catheter is vapor annealed in ethanol as described above (a).

Figure 2:
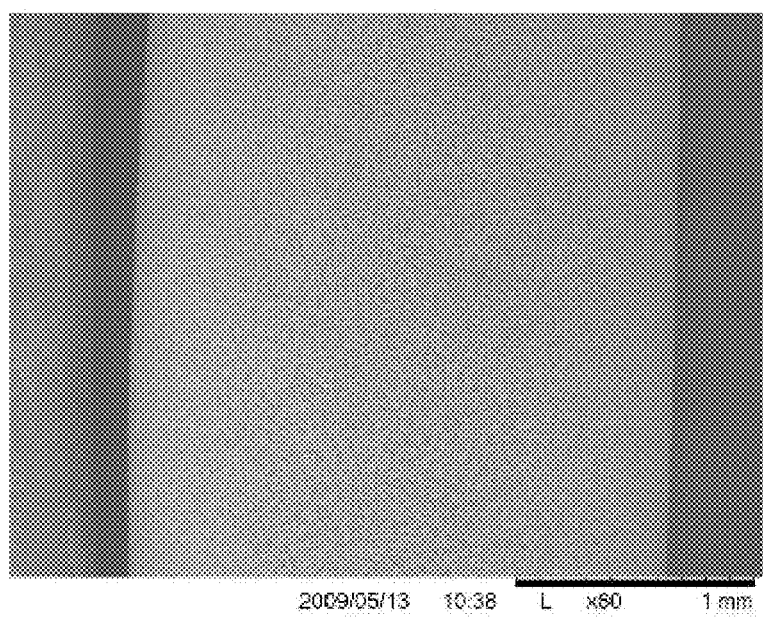
FIG. 2 is a magnified image showing a balloon made in accordance with one aspect of the invention.
Figure 3A:
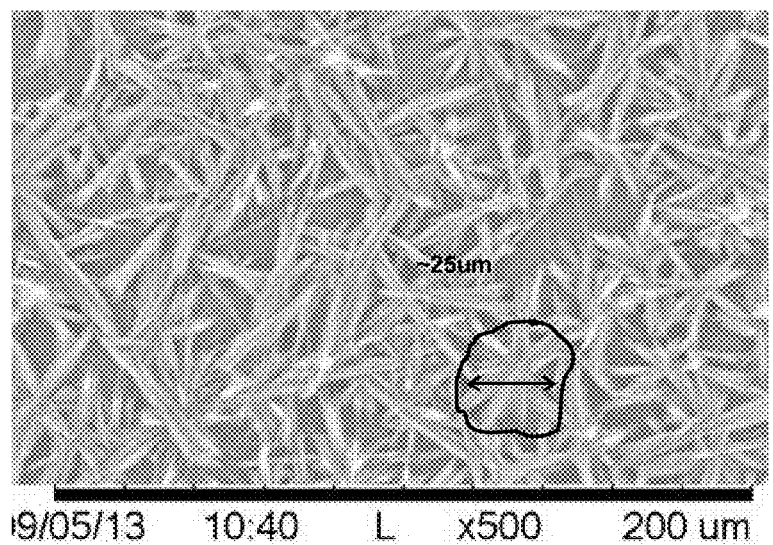
FIG. 3a is an SEM image of a portion of the balloon surface of the balloon of FIG. 2.
Figure 3B:
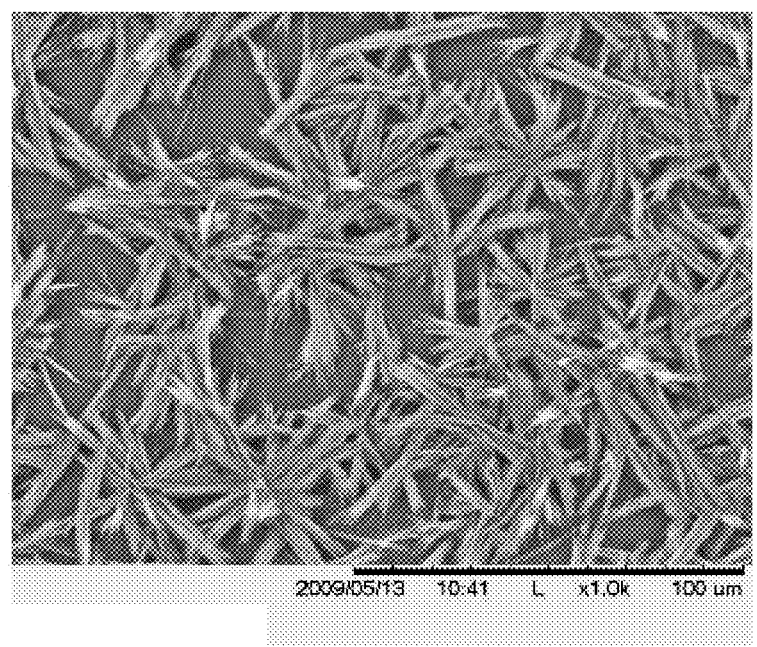

The crystals are rods or needles, often bunched and laid down in star-like or crossing pattern, with much shorter lengths, (10-60 μm length). FIG. 2 is an exemplary surface image, with FIGS. 3a and 3b providing illustrative magnified images depicting the "rod-like" structure of the crystalline particles.

Figure 6A:
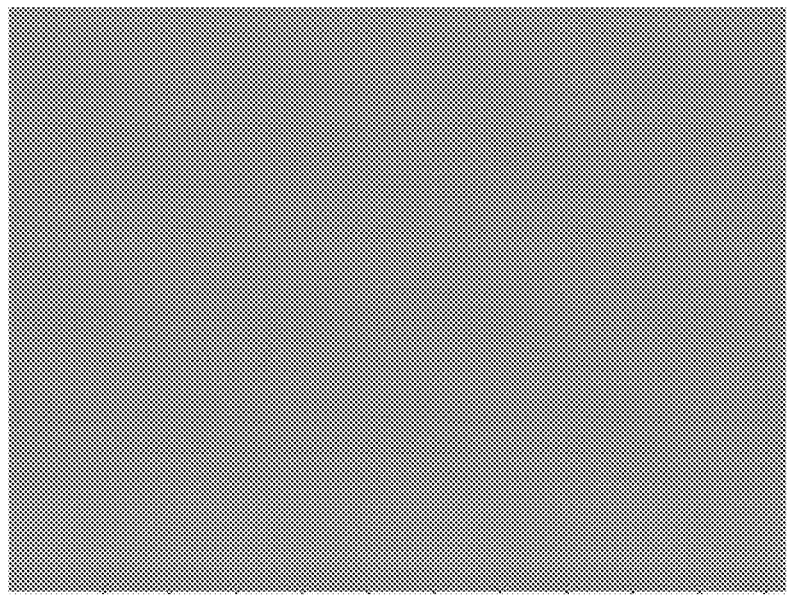
FIGS. 6a-6c are SEM images of Pebax® balloon surfaces after vapor pre-annealing for different time intervals.
Figure 6B:
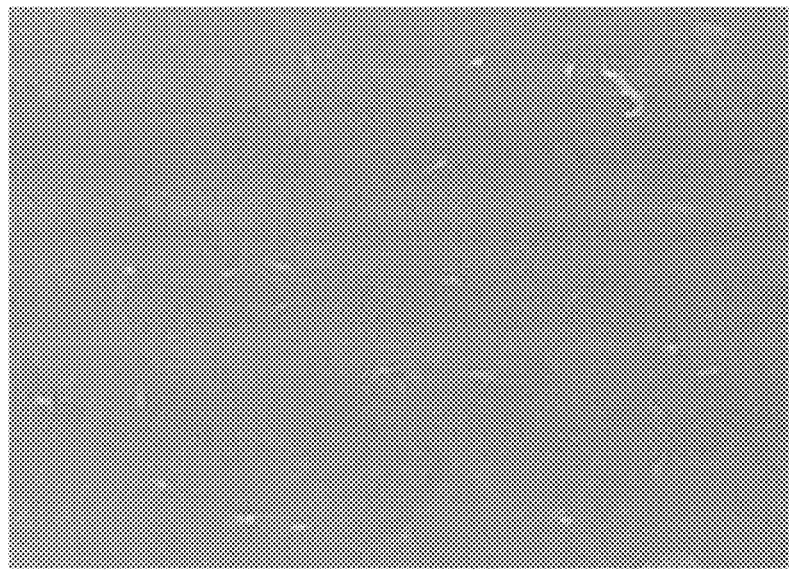
Figure 6C:

Reference is made to FIGS. 6a-6c, which are SEM images of the surface of a balloon made of Pebax® 7233, depicting the effect of the pretreatment of the balloon surface for 30 minutes, 1 hour and 16 hours respectively. FIG. 6a shows that after 30 minutes ethanol vapor anneal the balloon surface still has no visible topography. However blooming of lauryl lactam is visible in the 1 hour image (FIG. 6b), and is very well developed in the 16 hour image (FIG. 6c).

If a balloon is made of Pebax® 6333, which blooms lauryl lactam without solvent treatment, the rod-like morphology paclitaxel crystals are produced when an amorphous paclitaxel coating is subjected to vapor treatment, even without a vapor anneal pretreatment of the balloon. However, fan-like crystal morphology can be produced on Pebax® 6333 if the balloon is extracted with a solvent that dissolves lauryl lactam, for instance THF, and then the extracted balloon is processed as in Example 1a.

Figure 4:
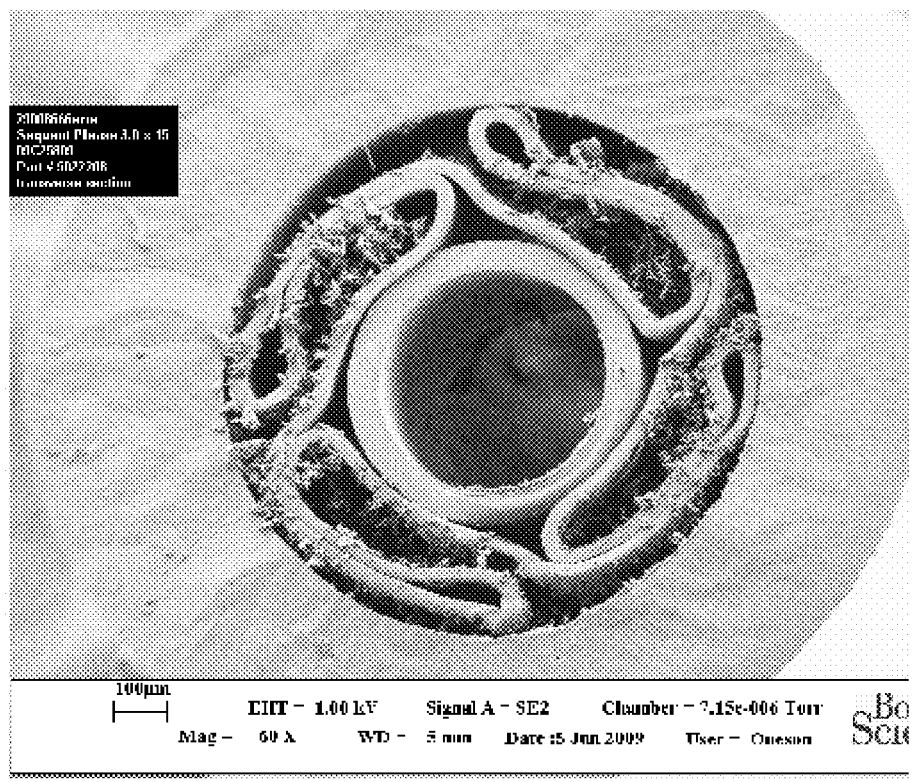
FIG. 4 is an SEM image of a cross-section of a commercial prior art Sequent Please™ catheter taken through the folded balloon.

FIG. 4 is an SEM image of a cross-section of a commercial prior art Sequent Please™ balloon catheter, sold by B. Braun, that has a paclitaxel/iopramide coating. The image is taken through the folded balloon and shows small rod-like crystals in the fold area, but they show very poor association with the surface and seem to have grown to loosely fill void space under the balloon folds, with many crystals extending outward from, rather than parallel to, the surface.

Figure 5A:
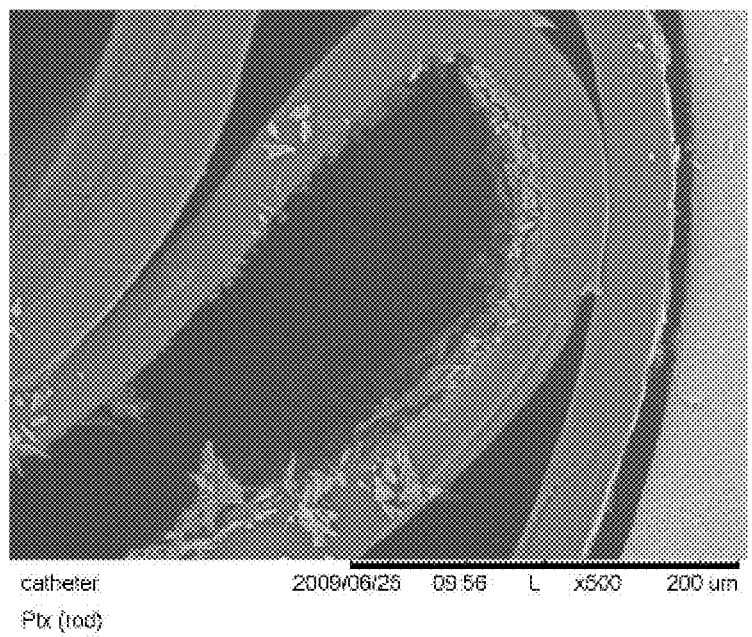
FIG. 5a is a cross-sectioned fold region of a balloon made in accordance with one aspect of the invention.

FIG. 5a depicts a cross-section through the fold of a balloon made in a manner of Example 1b above. It can be seen that the crystals of the coating are densely packed, particularity with respect to the plane of the balloon. The coating is thin (substantially under 10 μm) and is relatively robust due to the high density packing of the crystals parallel to the balloon surface.

Figure 5B:
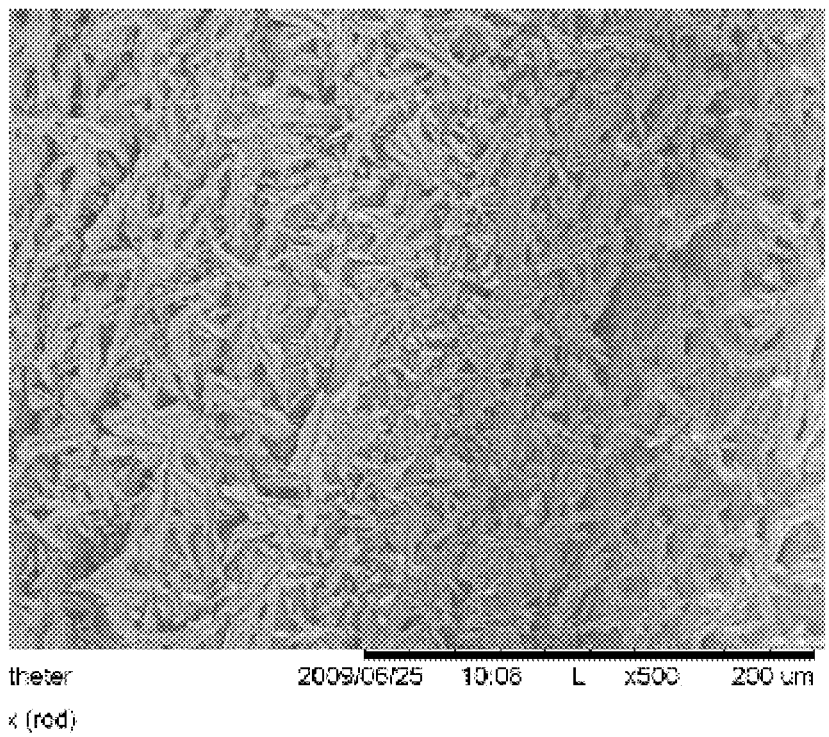

FIG. 5b depicts the surface of a balloon made in a manner of Example 1b above.

Figure 5C:
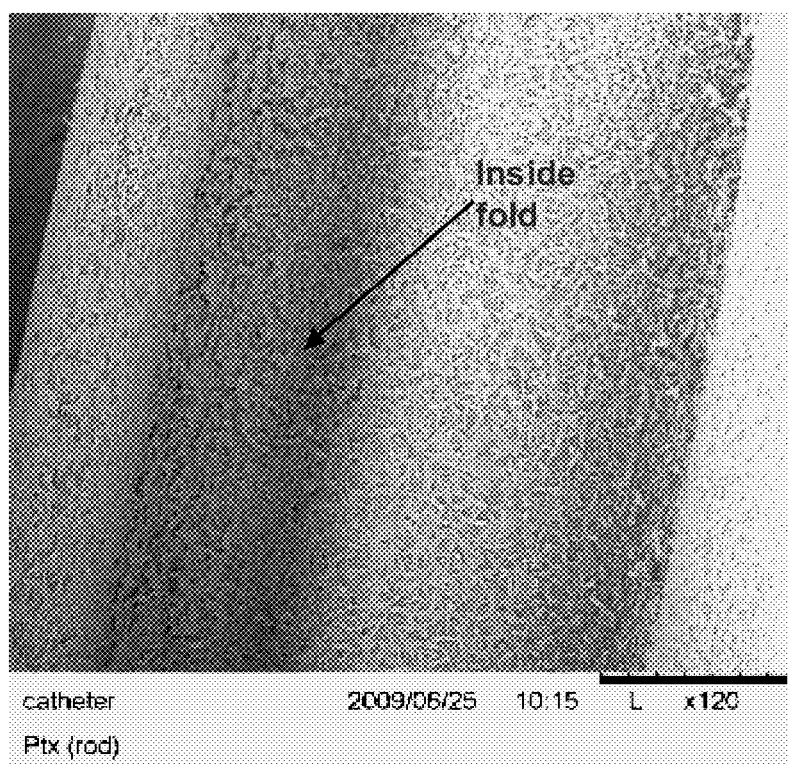
FIG. 5c is surface region of a balloon surface region made in accordance with one aspect of the invention at a lower magnification than FIG. 5b.

FIG. 5c depicts the surface of the balloon made in a manner of Example 1b after inflation from the folded state. Note the uniform crystal structure on the surface after inflation from the folded state.

Figure 7A:
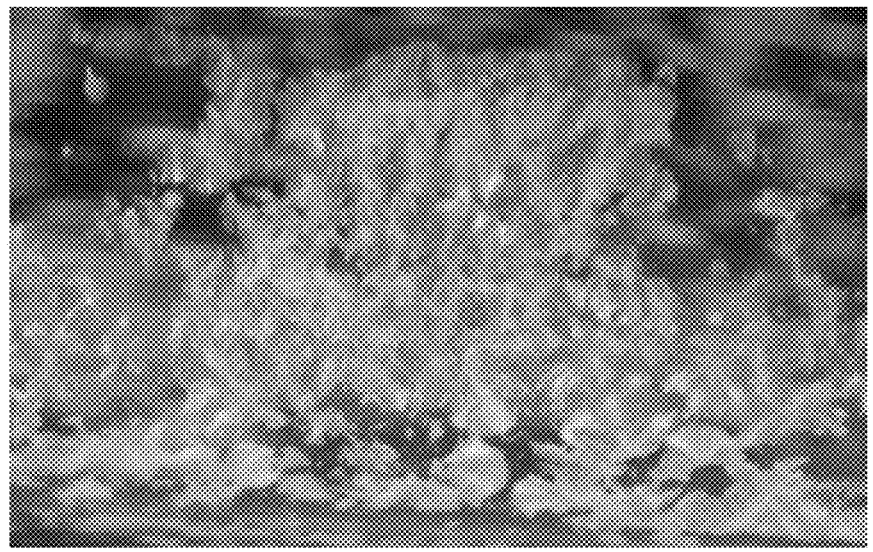
FIGS. 7a and 7b, respectively, are images of drug deployed in tubing from balloons with fan-like and rod-morphologies, as described in Example 2.

Example 2. Deployment in Tube of Large and Small Paclitaxel Crystalline Morphologies This example illustrates the impact of paclitaxel crystal size on in-vitro performance using the deployment in tube bench-top test. The balloon is folded and deployed in a hydrophilic polyurethane using the following procedure. The tube is placed in water at 37° C. The folded balloon is placed in the tube and inflated after soaking for 1 min. The tube is sized to give 20% overstretch during balloon deployment. Inflation is maintained for 1 minute, vacuum is pulled for 15 sec and the balloon is removed from the tube. The tube is removed from the water and dried and imaged. Images of the deployed drug on the tube are shown in FIGS. 7a and 7b.

Two crystal coating structures were tested. The balloon used to prepare FIG. 7a had large fan-like crystals similar to the balloon depicted in FIG. 1. The balloon used to prepare FIG. 7b had a small rod-like crystalline structure similar to that in FIGS. 3a and 3b.

Figure 7B:
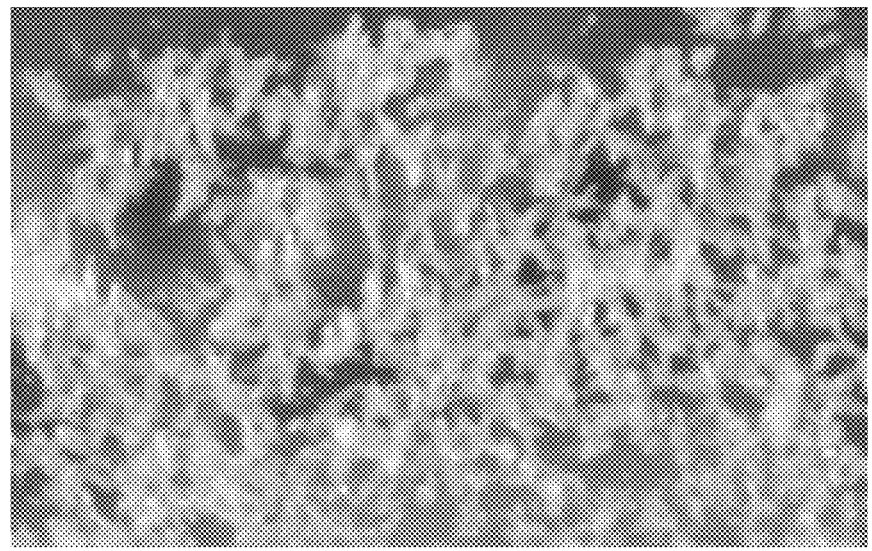

The balloon with large fan-like crystals transferred correspondingly large particles to the tube (FIG. 7a) compared to smaller drug particles apparent in FIG. 7b. It is considered that the smaller particles of the balloon with the rod-like particles will be safer with respect to coating released systemically in the course of tracking and deployment of these balloons.

Example 3. Particulate Testing

Figure 8A:
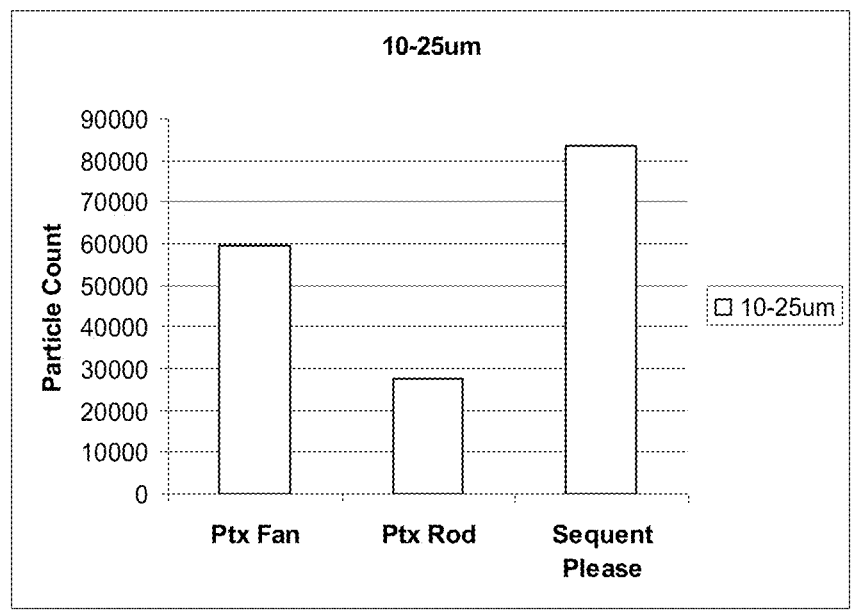
FIGS. 8a-8c are graphs the results of particle counts for various size ranges obtained in a flowing system experiment described in Example 3.
Figure 8B:
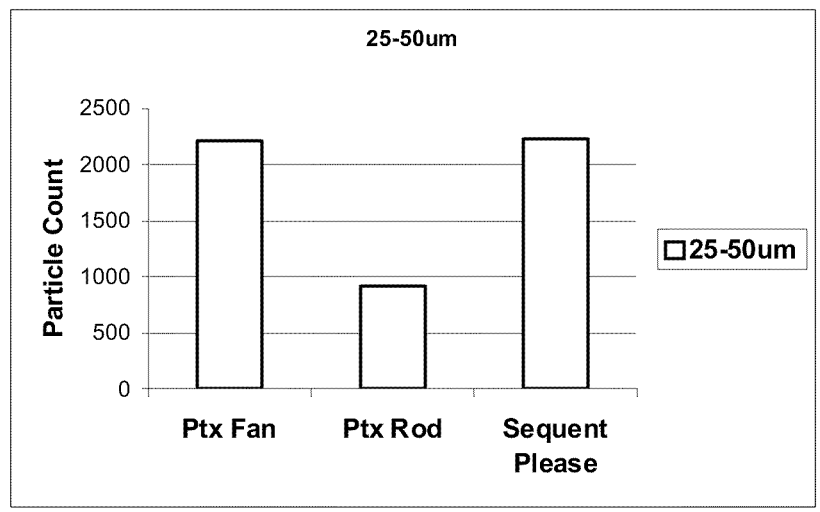
Figure 8C:
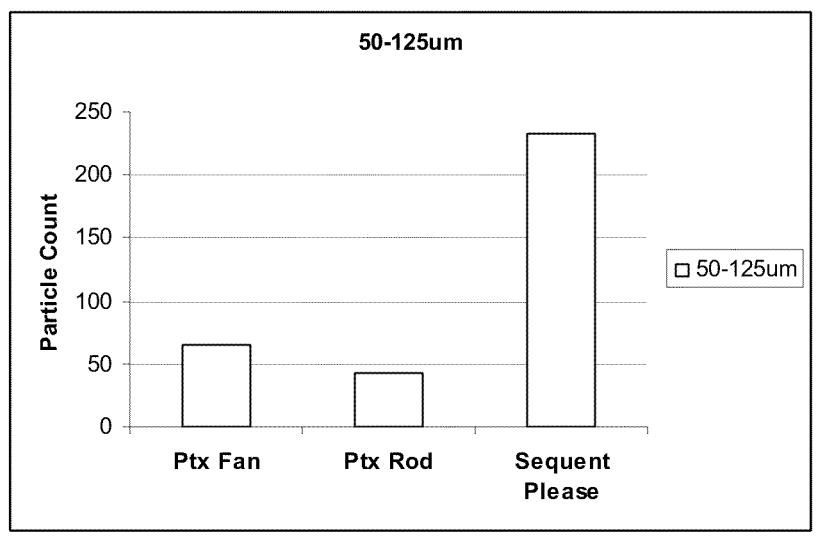

Particulate testing was performed on drug coated balloon catheters using the following method. The balloon catheter (N=3 for each design) was tracked through a curved glass artery model and into a hydrophilic polyurethane tube (artificial artery). The artery model is part of a closed loop system in which water flow is maintained during the test (flow rate: 70 ml/min). The flow loop is connected to a laser particle counter. Particle counts are taken while tracking the balloon to the polyurethane artery. Particle counts are taken for 2 min prior to deployment. The balloon is deployed for 30 sec at 12 atm. Particle counts are then taken over a 2 min period post-deployment. Total particle counts for 10-25 um, 25-50 um and 50-125 um particle size bins are measured. Three designs were tested. "Ptx Fan" was a paclitaxel coating (no excipient) with fan-like morphology on a Pebax® 7233 balloon prepared from an amorphous paclitaxel coating by post application vapor annealing of the coating. "Ptx Rod" was a paclitaxel (no excipient) with a rod-like morphology on a Pebax® 7233 balloon prepared by a vapor pre-treatment of the balloon, application of an amorphous paclitaxel coating and then post-treatment to crystallize the coating. "Sequent Please" was a prior art drug delivery balloon catheter sold by B. Braun with a paclitaxel/iopramide coating. All balloons had paclitaxel drug content of about 3 ug/mm$^2$. FIGS. 8a-8c show the particle count results. Of the two paclitaxel particle morphologies, the rod-like morphology gives fewer particles during track/deployment. Both paclitaxel morphologies (rod and fan) give significantly lower particle counts than the commercial comparative control. The result is considered to be indicative that forming a crystalline coating by crystallization of an amorphous coating via vapor annealing gives improved coating properties.

Example 4. Ex-Vivo Drug Tissue Levels

Figure 9:
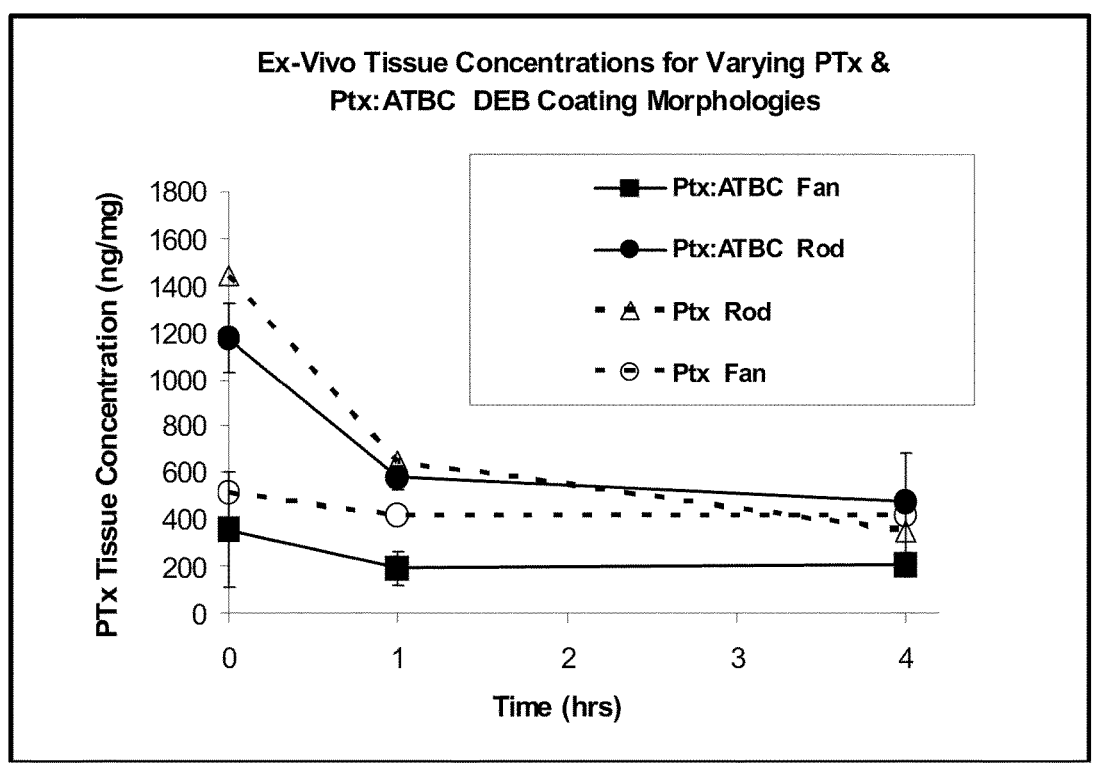
FIG. 9 is a graph of results of ex-vivo tissue concentrations found in a tissue deployment model experiment described in Example 4.

Drug coated balloon catheters were deployed (1 min inflation) in explanted porcine arteries under flow conditions at 37° C., 40 ml/min in media (80% Dubecco's Modified Eagle media; 20% Fetal Bovine Serum). Arteries were analyzed for total drug content via LC-MS after 0, 1 and 4 hrs post deployment. The following coating formulations were tested on Pebax® 7233 balloons: paclitaxel crystalline (fan-like); paclitaxel crystalline (rod-like); paclitaxel/acetyl tributyl citrate blend (85/15 wt/wt)—(fan-like); and paclitaxel/acetyl tributyl citrate blend (85/15 wt/wt) (rod-like). Drug content was approximately 3 ug/mm$^2$ for all formulations. Drug tissue results are shown in FIG. 9.

Both paclitaxel only (rod-like) and paclitaxel/ATBC (rod-like) crystalline morphologies show higher drug tissue levels compared to the corresponding paclitaxel only (fan-like) and paclitaxel/ATBC (fan-like) morphologies. Tissue levels of about 200 to about 600 ng/mg of drug in the tissue. after 4 hours deployment. The samples providing greater than about 300 ng/mg or greater than about 400 ng/mg are considered particularly advantageous.

The preceding examples show that paclitaxel crystal structure (fan & rod) impacts the number of particulates and tissue uptake. The rod like crystalline structure as described in this invention leads to fewer particles and higher tissue levels compared to the comparative commercial balloons taken as controls. Crystalline morphologies generated by vapor annealing have good adhesion to the balloon and good inter-crystal adhesion. Vapor annealing of a continuous integral amorphous drug coating results in solid state (or semi-solid) crystallization of the drug leading to crystalline coatings with the crystals oriented parallel to the balloon surface and robust crystal packing.

The devices of the present invention, may be deployed in vascular passageways, including veins and arteries, for instance coronary arteries, renal arteries, peripheral arteries including illiac arteries, arteries of the neck and cerebral arteries, and may also be advantageously employed in other body structures, including but not limited to arteries, veins, biliary ducts, urethras, fallopian tubes, bronchial tubes, the trachea, the esophagus and the prostate.

In some embodiments a drug coating of paclitaxel on a balloon contains from 100 to 1000 μg of paclitaxel, for instance 200-800 μg, 300-600 μg, or 400-500 μg of paclitaxel. In some embodiments the amount of amorphous paclitaxel on the balloon is from 0-80 μg, less than 60 μg, or less than 30 μg, with the remaining being a crystalline forms. The preceding paclitaxel wts are based on the effective surface area of a 3.0 mm×16 mm balloon. For other sizes, adjustments to provide the same weight of drug per unit area may be readily calculated.

In a vapor annealing step with 90-95% ethanol, the water content is sufficient to provide the dihydrate crystalline form within a very rapid time frame, for instance a few minutes. If it is desired to provide anhydrous crystalline paclitaxel a solvent with a lower water content may be used (for example 200 proof ethanol). In some embodiments the amount of anhydrous crystalline paclitaxel on the balloon (3.0 mm×16 mm) is from 0-200 µg, less than 100 µg, or less than 50 µg. In some embodiments the amount of crystalline dihydrate paclitaxel on the balloon is from 50 to 1000 µg, 100-800 µg, 200-600 µg, 300-500 or 350-450 µg. In some embodiments the fraction of amorphous paclitaxel in the coating is from 0-25%, for instance about 1%, about 2%, about 3%, about 5%, about 6%, about 8%, about 10%, about 12%, about 15%, about 18%, about 20%, about 22%, or about 25%, based on total paclitaxel weight. In some embodiments the fraction of anhydrous crystalline paclitaxel is from 0% to about 99%, for instance 1-95%, 5-80%, about 1%, about 2%, about 3%, about 5%, about 6%, about 8%, about 10%, about 15%, about 20%, about 25%, about 30%, about 40%, about 50%, about 60%, about 70%, or about 80%, based on total paclitaxel weight. In some embodiments the fraction of dihydrate crystalline paclitaxel is from 1% to 100%, for instance 1-99%, 5-95%, about 10%, about 15%, about 20%, about 25%, about 30%, about 35%, about 40%, about 45%, about 50%, about 55%, about 60%, about 65%, about 70%, about 75%, about 80%, about 85%, about 88%, about 89%, about 90%, about 91%, about 92%, about 93%, about 94%, about 95%, about 96%, about 97%, about 98%, or about 99%, based on total paclitaxel weight.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

The invention claimed is:

1. A method of making a drug delivery balloon having a coating thereon comprising a drug, the balloon made of a balloon material, the drug selected from the group consisting of paclitaxel, paclitaxel analogs and paclitaxel derivatives, wherein the drug has a characteristic amorphous form and a crystalline form comprising:
   a) applying a coating of the drug in the amorphous form to the balloon material, and, subsequent to applying the coating,
   b) annealing with a solvent vapor the coating which has been applied in step a), the solvent vapor comprising an alcohol, to produce the crystalline form of the drug on the balloon,
   wherein in the applying step a) the drug coating is applied to a balloon surface that has been nucleated by blooming of a component in the balloon material to the surface thereof, the component crystallizing at the surface of the balloon material as a result of the blooming to induce formation of drug crystals in the annealing step.

2. A method as in claim 1 wherein the coated balloon is annealed in step b) with a solvent vapor.

3. A method as in claim 2 wherein the solvent vapor comprises an alcohol and water.

4. A method as in claim 1 wherein said blooming is facilitated by a pretreatment of the balloon surface prior to applying the drug coating.

5. A method as in claim 4 wherein said pretreatment comprises a solvent vapor annealing of the balloon.

6. A method as in claim 1 wherein the balloon material comprises a polyamide block copolymer.

7. A method as in claim 1 wherein the drug is applied to the device as a formulation with an excipient.

8. Method as in claim 7 wherein said excipient is a member of the group consisting of water soluble polymers, sugars, contrast agents, citrate esters, glycerol esters of short chain monocarboxylic acids and pharmaceutically acceptable salts.

9. A method as in claim 2 wherein in the annealing step the balloon is placed in an annealing chamber in which the solvent vapor, at the time the balloon is put into the chamber, is at a vapor pressure that is less than saturation at the temperature and pressure of the chamber.

10. A method as in claim 2 wherein the in the annealing step the solvent vapor is provided in an annealing chamber having a chamber volume to solvent surface ratio in the range of from about 35-75 ml/cm$^2$.

11. A method as in claim 1 wherein the balloon surface is nucleated with particulate nucleating agent on the surface of the balloon, said particulate nucleating agent having a major dimension in the size range of from about 10 nm to about 20 µm.

12. A method as in claim 11 wherein the particulate nucleating agent has a density on the balloon of from about 10 particle/mm$^2$ to about 5000 particles/mm$^2$.

13. A method as in claim 11 wherein the particulate nucleating agent has a density on the balloon of from about 100 particles/mm$^2$ to about 2000 particles/mm$^2$.

14. A method as in claim 1 wherein the drug is paclitaxel.

15. A method as in any one of claims 1-3 and 4-6 wherein the drug is applied to the device as a formulation without an excipient.

16. A method as in claim 1 wherein in the applying step a) the nucleation of the balloon surface provides a controlled distribution of drug crystals in the annealing step.

17. A method of making a drug delivery balloon having a coating thereon comprising a drug, the balloon made of a balloon material, the drug selected from the group consisting of paclitaxel, paclitaxel analogs and paclitaxel derivatives, wherein the drug has a characteristic amorphous form and a crystalline form comprising:
- a) applying a coating of the drug in the amorphous form to the balloon material, and, subsequent to applying the coating,
- b) annealing with a solvent vapor the coating which has been applied in step a), the solvent vapor comprising an alcohol, to produce the crystalline form of the drug on the balloon, wherein in the applying step the drug coating is applied to a balloon surface that has been nucleated by treating the balloon material so as to cause a component from within the balloon material to migrate to the surface of the balloon material, the component crystallizing at the surface of the balloon material and inducing formation of drug crystals in the annealing step.

* * * * *